United States Patent [19]

Fung

[11] Patent Number: 5,969,120

[45] Date of Patent: Oct. 19, 1999

[54] MUTANTS OF THE RB AND P53 GENES

[75] Inventor: Yuen Kai Fung, Los Angeles, Calif.

[73] Assignee: Research Development Foundation, Carson City, Nev.

[21] Appl. No.: 08/372,100

[22] Filed: Dec. 23, 1994

Related U.S. Application Data

[63] Continuation-in-part of application No. 08/116,943, Sep. 3, 1993, abandoned.

[51] Int. Cl.⁶ .............................. C12N 15/11; C12N 15/63
[52] U.S. Cl. ...................... 536/23.1; 536/23.5; 435/320.1
[58] Field of Search .................................. 536/23.1, 23.5; 435/320.1, 69.1, 172.3

[56] References Cited

FOREIGN PATENT DOCUMENTS

WO 89/06703   7/1989   WIPO .

OTHER PUBLICATIONS

Schulz et al., Principles of Protein Structure, Springer–Verlag, New York, pp. 14–16, 1979.

Lewin, Genes II, John Wiley and Sons, New York, p. 96, 1985.

Kern et al. 1991. Oncogene 6:131–6.

Bowie et al. 1990. Science 247:1306–10.

Friedmann. 1992. Cancer 70:1810–7.

Jain. 1994. Sci. Amer. 271(1):58–65.

Gutierrez et al. 1992. The Lancet 339:715–721.

Curti. 1993. Crit. Rev. Oncology/Hematology 14:29–39.

*Primary Examiner*—Elizabeth Kemmerer
*Attorney, Agent, or Firm*—Benjamin Aaron Adler

[57] ABSTRACT

The present invention provides mutants of the Rb and p53 genes and methods utilizing these mutants therapeutically. Along with mutated Rb genes and p53 genes, the present invention provides plasmids containing a mutated Rb gene or a p53 gene. In addition, the present invention provides cells transfected with the plasmids of the present invention. Moreover, the present invention provides for methods of treating a variety of pathophysiological cell proliferative diseases.

2 Claims, 15 Drawing Sheets

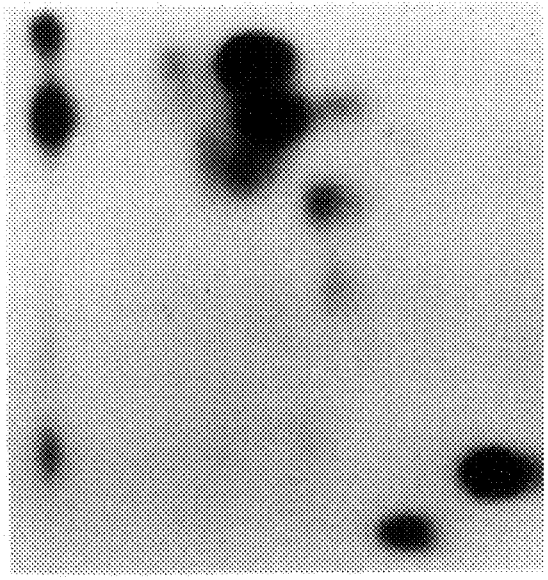 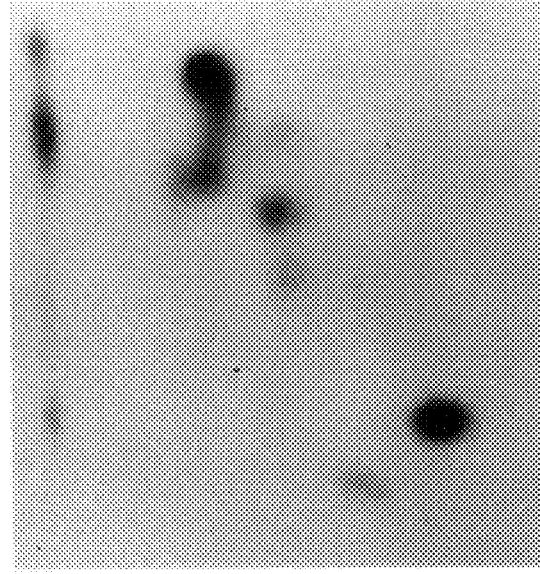
Untreated
TGFß treated
For 48 hours
FIGURE 7A
FIGURE 7B

Wild type ( Domain F hidden, Domain R exposed )

Mutant ( Domain F exposed, Domain R hidden )

MUTANTS OF THE RB AND P53 GENES

CROSS-REFERENCE TO RELATED APPLICATION

This application is a continuation-in-part of U.S. patent application Ser. No. 08/116,943, filed Sep. 3, 1993, now abandoned.

BACKGROUND OF THE INVENTION

1. Field of the Invention

The present invention relates generally to the field of regulation of cell growth and proliferative diseases. More specifically, the present invention relates to mutants of the RB-1 and p53 genes and therapeutic uses of such mutants.

2. Description of the Related Art

The control of cell proliferation is a complex process which involves multiple interacting components. Whether a cell grows or not depends on the balance of the expression of negatively-acting and positively-acting growth regulatory genes. Negatively-acting growth regulatory genes are those that, when expressed in or provided to a cell, lead to suppression of cell growth. Positively-acting growth regulatory genes are those which, when expressed in or provided to a cell, stimulate its proliferation.

Recently, several negatively acting growth regulatory genes called tumor suppressor genes which have a negative effect on cell proliferation have been identified. These genes include, but are not limited to, the human retinoblastoma gene, RB-1, and the p53 gene. The absence or inactivation of some of these negative growth regulatory genes has been correlated with certain types of cancer.

The human retinoblastoma gene, RB-1, is the prototype of this class of tumor suppressor genes in which the absence of both alleles of the gene in a cell or the inhibition of the expression of the gene or its gene product will lead to neoplastic or abnormal cellular proliferation. At the molecular level, loss or inactivation of both alleles of RB-1 is involved in the clinical manifestation of tumors such as retinoblastoma and clinically related tumors, such as osteosarcomas, fibrosarcomas, soft tissue sarcomas and melanomas. In addition, loss of the function of RB-1 has also been associated with other types of primary cancer such as primary small cell lung carcinoma, bladder carcinoma, breast carcinomas, cervical carcinomas and prostate carcinomas.

The Tumor Suppressor Genes Rb and p53 suppress the proliferation of cancerous and noncancerous cells The re-introduction of a wild-type cDNA of RB-1 or p53 have been shown to partially restore normal growth regulation as the re-introduced genes induce growth arrest or retardation in many different tumor cell types. The designation of the Rb gene as a tumor suppression gene stemmed from the fact that inactivation of an allele of the Rb gene is a predisposition to the development of cancer. However, the growth suppression effect of the Rb gene is not restricted to tumor cells. Normal cells which have two copies can be growth arrested or retarded by the introduction of extra copies of the Rb gene under certain growth conditions. Likewise, the ability of a wild type p53 to suppress the growth of noncancerous cells is well documented. Thus, the step controlled by Rb and p53 may not directly affect the tumorigenic phenotype but rather the steps that control the growth of tumor and normal cells alike are affected.

Mechanisms of pathological proliferation of normal cells

There is a wide variety of pathological cell proliferative conditions for which novel methods are needed to provide therapeutic benefits. These pathological conditions may occur in almost all cell types capable of abnormal cell proliferation. Among the cell types which exhibit pathological or abnormal growth are (1) fibroblasts, (2) vascular endothelial cells, and (3) epithelial cells. It can be seen from the above that methods are needed to treat local or disseminated pathological conditions in all or almost all organ and tissue systems of the individual.

For instance, in the eye alone, novel methods may be utilized to treat such a wide variety of pathologic disease states which are due to abnormal proliferation of normal, benign or malignant cells or tissues including, but not limited to, the following: fibroproliferative, vasoproliferative and/or neoplastic diseases of the eye: retinopathy of prematurity, proliferative vitreoretinopathy, proliferative diabetic retinopathy, capillary hemangioma, choroidal neovascular nets, subretinal neovascular nets, senile macular degeneration due to subretinal, neovascularization, corneal neovascularization, macular pucker due to epiretinal membrane proliferation, adult cataracts due to nuclear sclerosis, fibrous ingrowth following trauma or surgery, optic nerve gliomas, angiomatosis retinae, neovascular glaucoma, cavernous hemangioma, rubeosis iridis, sickle cell proliferative retinopathy, epithelial downgrowth after eye surgery or injury, after-cataract membrane, papilloma, retinal neovascularization in thalassemia, subretinal neovascularization due to pseudoxanthoma elasticum, and neurofibromatosis type 1 and 11, retinoblastoma, uveal melanoma, and pseudotumor of the orbit. Other benign cell proliferative diseases for which the present invention is useful include, but are not limited to, psoriasis, ichthyosis, papillomas, basal cell carcinomas, squamous cell carcinoma, and Stevens-Johnson Syndrome.

It should be noted that in the case of normal cells, there are already two normal alleles each of the Rb gene and the P53 gene and yet these wild type proteins fail to prevent the cells from proliferating when the cells were provided growth factors, as for example in tissue culture growth conditions. The uncontrolled proliferation of otherwise resting cells in pathological conditions is also due to the exposure of the cells to growth factors induced by the pathological conditions (see below). For an example, uncontrolled proliferation of blood vessels in the eye in thalassemia can lead to detachment of the retina if the proliferation is not stopped. The introduction of extra copies of the Rb gene or the P53 gene into such cells may or may not be sufficient to suppress the cells from growing. In fact, the introduction of exogenous Rb gene into many tumor cells only retarded the growth rate of the cells instead of complete arrest. The previously reported cell lines such as Saos-2 and DU145 are good examples of this phenomenon. Many more copies of the gene may need to be introduced and it is difficult to control on the one hand the number of copies that need to be or could be introduced. On the other hand, growth factor exposure may lead to inactivation of the expressed Rb proteins.

Regulation of the Activity of Rb Protein by Phosphorylation

If the inactivation of growth suppressor genes is an essential step in the removal of the constraint on cell growth, there must be mechanisms whereby the activities of these gene products are regulated so that a cell may proliferate in a controlled manner. It is conceivable that the expression of a given growth suppressor gene may be regulated quantitatively or qualitatively. In the case of the Rb gene, the ratio of the steady state level of the protein to the cell volume is a constant throughout the cell cycle. This lack of variation of the Rb protein concentration suggests that there must be other mechanisms whereby a cell can regulate the activity of this protein. There are several lines of evidence to show that the activity of the Rb protein (pRb) is regulated by its phosphorylation state. Various growth stimulatory or inhibitory factors exert their effects by perturbing the phosphorylation of growth suppressor gene products such as the Rb protein. Evidence for a role of growth stimulatory factors in the induction of phosphorylation of the Rb proteins have come from the observation that the Rb proteins exist in the underphosphorylated forms in quiescent cells. In addition, when quiescent cells were stimulated to proliferate by exposure either to serum or to growth factors such as EGF together with insulin and transferrin, the predominant form of the Rb protein was underphosphorylated in G1 but became hyperphosphorylated as the cells enter the G1/S boundary and the cells. These data suggest that the Rb protein is a target of the signal transduction pathway induced by serum or growth factors. Finally, senescent human fibroblast cells incapable of responding to the proliferation stimulatory effects of growth factors also failed to phosphorylate the Rb protein.

There are also evidence for a role of growth inhibitory factors in the downregulation of phosphorylation of the Rb proteins. When actively growing leukemia or neuroblastoma cells were treated with retinoic acid or vitamin D3, DMSO other differentiation inducing reagents, the Rb proteins were found to be underphosphorylated prior to the on set of cell growth arrest in the early G1 phase and induced to differentiation. In addition, the treatment of lung epithelial cells with the paracrine growth inhibitory polypeptides-transforming growth factor Beta 1 (TGFβ-1) led to the downregulation of phosphorylation of the Rb protein and concomitant arrest of cell growth in late G1. Taken together, these data suggest the underphosphorylated form of the Rb protein actively suppressed cells from traversing the G1/S boundary and that a kinase (S), activated in G1, can inactivate the Rb protein so that the cells may move into the S phase.

While the permanent removal of the Rb gene, by deletion or mutation, in tumor cells allowed growth, removal of the constraint on growth in normal cells having normal expression of the Rb gene is achieved by cell cycle dependent post-translational modification of its gene product, i.e., the Rb protein (pRb). The Rb protein exists in multi-phosphorylated forms and evidence suggests that the underphosphorylated form is the active form. For example, the SV40 large T antigen preferentially binds to the underphosphorylated form of the Rb protein. Phosphorylation of the Rb protein releases it from the SV40 large T antigen and only the underphosphorylated forms of pRb binds to and inhibits transcription from the E2 promotor. Thus, the underphosphorylated form of the Rb protein actively suppresses cell growth, whereas cell proliferation is associated with hyperphosphorylation of the Rb protein. Various growth stimulatory or inhibitory factors may exert their effects by perturbing the phosphorylation of the Rb protein. Therefore, although a normal cell may be expressing the Rb proteins, it can be induced to grow when exposed to appropriate growth factors such as may be found in various growth conditions, including pathological conditions. Under certain pathological conditions, an otherwise normal cell may be induced to proliferate undesirably. Proliferation of normally quiescent fibroblasts in the eyes in diabetic retinopathy is an example of such unwanted induction of cell growth. Left untreated, the proliferating fibroblasts will eventually attach to the retina and lead to its rapid detachment.

Activation of the p53 protein

Similar to the Rb gene, inactivation or mutation of the p53 gene has been frequently observed in tumor and nontumorous cell lines. Wild type p53 protein is also negatively regulated when it binds to viral antigens such as the SV40 large T. The p53 protein functions as a transcription factor and binds to specific DNA sequences. The ability of the wildtype p53 protein to bind DNA is critical for it to function properly. In mutant p53, the ability of the protein to bind to specific DNA target sequences or to activate transcription is lost, suggesting that these activities are importantant for the suppressive function of the protein. However it has also been recently shown that sequence specific DNA binding activity of the p53 protien is cryptic. Newly synthesized p53 protien is innactive in that it cannot bind to its specific DNA sequence unless the protein is modified. One of the sites for modification is amino acid residues 365–393 at the C-terminus. This region is the site for the attachment of an RNA moiety as well as for the binding to the bacterial heat shock proteins dnaK. Binding of an antibody, Pab421, to the 365–389 amino acid residues activates the protein by altering its conformation so that it can bind to its specific DNA sequence.

Difference in the mode of function of pRb and p53 although both Rb and p53 are regarded as tumor suppressor genes, their modes of action are very different. Previously, evidence was provided that these two genes may work on different pathways. Mice null for the Rb gene is embryonically lethal while mice null for p53 develop normally although they are more susceptible to cancer development. At the cellular level, cancer cells that are devoid of p53 can be growth arrested or retarded by the overexpression of the Rb gene even in the absence of exogenous p53. On the other hand, cells devoid of Rb are susceptible to the growth suppression effect of the p53 gene. At the molecular level, p53 and pRb interacts with different protein targets and DNA sequences (directly or indirectly).

The use of the Rb and p53 gene in therapy

While these two proteins are different in their modes of action, they are similar in one aspect, i.e., overexpression of the active forms of the two proteins under experimental conditions lead to the suppression or retardation of growth of cells. Knowing that cell growth is controlled by the expression of suppressor genes such as pRb and p53 and that their proteins need to be in the active conformations in order to function, it is desirable to have active forms of these genes for gene therapy. In the case of pRb, the newly synthesized proteins are underphosphorylated and are active. Inactivation may occur as the cells are exposed to growth factors. It would be desirable to have mutant forms of pRb that would remain in the active form and are resistant to inactivation by phosphorylation. In the case of p53, the newly synthesized protein is inactive in that it cannot bind DNA unless modified. In gene therapy, it would be highly desirable to have mutant forms of the p53 gene, the protein of which is already active even without further modification. Finally, since the two proteins have different modes of action, it would be desirable to use a combination of both the Rb and the p53 genes in therapy such that the mutations or growth conditions that renders a cell resistant to the growth suppression effect of one gene may be susceptible to the other.

The prior art remains deficient in the lack of a tumor suppressor gene mutated so that the gene product (protein) is permanently active and can function even when the cell is exposed to growth factors. More specifically, the prior art is deficient in the lack of effective and functional mutated forms of the p53 and Rb genes. The prior art also remains deficient in the simultaneous application of the wildtype and/or the mutant forms of the Rb and the p53 genes in cancerous and noncancerous cell proliferative diseases.

SUMMARY OF THE INVENTION

In one aspect, the present invention provides a generalized approach to the treatment of inappropriate or pathological cell growth such as exists in non-cancerous cell proliferative diseases as well as cancerous cell proliferative diseases. More specifically, the present invention provides methods of treating pathophysiological cell proliferative diseases by administering mutated growth suppressor gene and/or gene products, i.e., mutated proteins.

In one embodiment of the present invention, there is provided an isolated DNA molecule, wherein said molecule is a synthetic mutated Rb gene encoding a mutated functionally active retinoblastoma protein.

In another embodiment of the present invention, there is provided an isolated DNA molecule, wherein said molecule is a synthetic mutated p53 gene encoding a mutated functionally active p53 protein.

In another embodiment of the present invention, there is provided a novel plasmid containing a functionally active mutant of the retinoblastoma or p53 gene.

In yet another embodiment of the present invention, there is provided a method of the consecutive or simultaneous administration of the wild type and/or the active mutants of both the Rb and the p53 genes for therapeutic purposes.

In other embodiments of the present invention, there are provided methods for the treatment of pathological cell proliferative diseases comprising administration concurrently or consecutively to a non-cancerous proliferating cell a mutated Rb gene and a mutated P53 gene.

Additionally provided is a method of treating malignant cell diseases in individuals comprising administration concurrently or consecutively into a proliferating cancer cell of a mutated Rb gene and a mutated P53 gene.

In yet another embodiment of the present invention, there is provided a method of inducing apoptosis, comprising the step of administering the mutant p53 protein of the present invention to a cell.

In yet another embodiment of the present invention, there is provided a method of treating a tumor cell having a mutation of a cyclin protein, comprising the step of administering the protein of claim 39 to a cell.

Other and further aspects, features, and advantages of the present invention will be apparent from the following description of the presently preferred embodiments of the invention given for the purpose of disclosure.

BRIEF DESCRIPTION OF THE FIGURES

FIGS. 7A and B show the two dimensional mapping analysis of the change in the phosphorylation pattern of the retinoblastoma protein under different growth conditions.

FIG. 13A shows that p53 mutants of the p3 or p5 homology region at the conserved aminoacids is active in promoting transcriptional activation.

FIG. 14A, wild type p53 without cisplatin; FIG. 14B, wild type p53+cisplatin; FIG. 14C, P4 p53 mutant without cisplatin; FIG. 14D, P4 p53 mutant+cisplatin; FIG. 14E, P5 p53 mutant without cisplatin; FIG. 14F, P5 p53 mutant+cisplatin.

DETAILED DESCRIPTION OF THE INVENTION

Definitions

Figure 1:
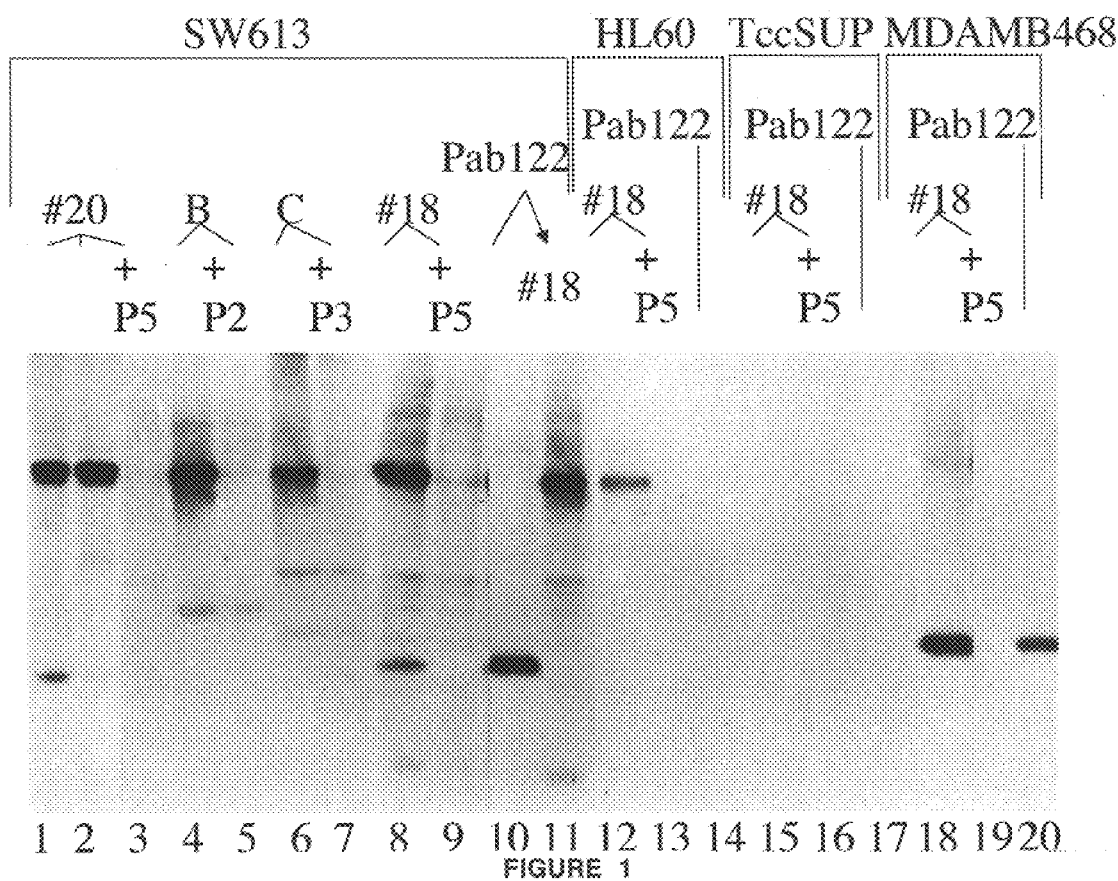
FIG. 1 shows the discovery of the homology region between pRb and p53 by immunoprecipitation of cellular proteins using polyclonal anti-Rb antibodies RB1-Ab #18 and #20.

The term "functional expression of the gene" meant to include the suppression of transcription of the gene, the degradation of the gene transcript (pre-message RNA), the inhibition of splicing, the destruction of the message RNA, the prevention of translation of the message RNA, the prevention of the post-translational modifications of the protein, the destruction of the protein, or the inhibition of the normal function of the protein.

The term "transfected plasmid" is meant to include the bacterial plasmid which contains a mutated retinoblastoma or p53 gene to be carried (transfected) into the cell of choice.

The term"gene therapy" is meant to include the insertion of part or all of a gene, a DNA construct, RNA, or gene product into a cell, group of cells, tissue, pathologic lesion, organ or organism for the purpose of modulating gene expression, and/or function of the gene product.

The term "prophylactic gene therapy" is meant to include genes which may be used for partial or total inhibition or prevention of disease and the spread of disease and also is meant to include genes which may be used to supplement or replace absent or defective negative growth in cell, tissues or germlines.

The term "cell proliferative disease" is meant to include any human or animal disease or disorder, affecting any one or any combination of organs, cavities or body parts, which is characterized by single or multiple local abnormal proliferations of cells, groups of cells or tissue(s), whether benign or malignant.

The term "prokaryote" is meant to include all bacteria which can be transformed with the DNA for the expression of the recombinant molecules of the present invention.

The term "eukaryote" is meant to include all yeasts, fungi, animal and plant cells which can be transformed with the DNA for the expression of the recombinant molecules of the present invention.

The DNA for DNA constructs of the present invention can be synthetic or may be derived from any mammalian species. All that is required is that the genetic sequence for the Rb or p53 genes be functionally expressed in the prokaryotic or eukaryotic organism. Preferred is synthetic DNA.

A recombinant DNA molecule coding for the DNA constructs of the present invention can be used to transform a host using any of the techniques commonly known to those of ordinary skill in the art.

Methods for preparing fused, operably linked genes and expressing them in bacteria are known and are shown, for example, in U.S. Pat. No. 4,366,246, herein incorporated by reference. The genetic constructs and methods described therein can be utilized for construction of the DNA constructs of the present invention and transfection in prokaryotic or eukaryotic hosts.

Prokaryotic hosts may include Gram negative as well as Gram positive bacteria, such as *E. coli, S. tymphimurium, Serratia marcescens* and *Bacillus subtilis*. Eukaryotic hosts may include yeasts such as *Pichia pastoris* or mammalian cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Examples of promoters which can be used in the invention include, but are not limited to: human 62-actin promotor, metallothionin promotor, SV40 origin of replication, MMTV LTR promotor and MuLV LTR promotor. Examples of some of the plasmids or bacteriophage which can be used in the invention are listed in Maniatis et al., *Molecular Cloning*, Cold Spring Harbor Laboratories, 1982, and others are known to those of skill in the art and can be easily ascertained.

A gene is a DNA sequence which encodes through its template or messenger RNA a sequence of amino acids characteristic of a specific peptide. The term cDNA includes genes from which the intervening sequences have been removed. The term "recombinant DNA" (rDNA) is meant to include a molecule that has been recombined by splicing cDNA or genomic DNA sequences in vitro.

A cloning vehicle is a plasmid or phage DNA or other DNA sequence which is able to replicate in a host cell which is characterized by one or a small number of endonuclease recognition sites at which such DNA sequences may be cut in a determinable fashion without loss of an essential biological function of the DNA, and which contains a marker suitable for use in the identification of transformed cells. Markers, for example, are tetracycline resistance or ampicillin resistance. The word "vector" is sometimes used for a cloning vehicle.

An expression vehicle is a vehicle similar to a cloning vehicle but which is capable of expressing a given structural gene in a host, normally under control of certain control sequences.

The term "individual" is meant to include animals and humans.

The term "biologically inhibiting" or "inhibition" of the growth of proliferating cells is meant to include partial or total growth inhibition and also is meant to include decreases in the rate of proliferation or growth of the cells. The biologically inhibitory dose of the mutants of the present invention may be determined by assessing the effects of the test element on target malignant or abnormally proliferating cell growth in tissue culture, tumor growth in animals and cell culture or any other method known to those of ordinary skill in the art.

As used herein, the term "conserved homology region" refers to that amino acid region that is homologous between Rb and p53 as illustrated in Table I.

Administration of the proteins of the present invention may be by topical, intraocular, parenteral, oral, intranasal, intravenous, intramuscular, subcutaneous, or any other suitable means. The preferred method of administration for treatment of ocular diseases is intraocular or periocular injection. The preferred method of administration for treatment of skin cell proliferative diseases is by topical application or subcutaneous injection.

In another embodiment, the DNA constructs of the present invention may be delivered to the focal proliferative disease directly. In the case of ocular proliferative disease, the DNA constructs of the present invention may be directly injected into the eye. The DNA constructs of the present invention may be delivered directly to focal disease sites in internal organs, body cavities and the like by use of imaging devices used to guide the injecting needle directly to the disease site. The DNA constructs of the present invention may also be administered to disease sites at the time of surgical intervention.

The DNA dosage administered is dependent upon the age, clinical stage and extent of the disease or genetic predisposition of the individual, location, weight, kind of concurrent treatment, if any, and nature of the pathological or malignant condition. The effective delivery system useful in the method of the present invention may be employed in such forms as capsules, tablets, liquid solutions, suspensions, or elixirs, for oral administration, or sterile liquid forms such as solutions, suspensions or emulsions. Any inert carrier is preferably used, such as saline, or phosphate-buffered saline, or any such carrier in which the compounds used in the method of the present invention have suitable solubility properties.

Preferably, for intraocular delivery and for delivery to other localized disease sites, delivery systems useful in the method of the present invention may be employed in such sterile liquid forms such as solutions, suspensions or emulsions. For topical use it may be employed in such forms as ointments, creams or sprays. Any inert carrier is preferably used, such as saline, or phosphate-buffered saline, or any such carrier in which the compounds used in the method of the present invention have suitable solubility properties.

For local administration to cells, administration may be by any method known to those of skill in the art including, but not limited to, transfection, electroporation, microinjection of cells, or in vehicles such as liposomes, lipofectin or as naked DNA or RNA. The DNA of the present invention may be delivered by known gene delivery systems such as, but not limited to, retroviral vectors (Gilboa (1982) J.

Virology 44:845; Hocke (1986) Nature 320:275; Wilson et al., Proc Natl Acad Sci USA 85:3014), vaccinia virus system (Chakrabarty et al., (1985) Mol. Cell Biol. 5:3403) or other efficient DNA delivery systems (Yates et al., (1985) Nature 313:812) known to those of skill in the art. These references are exemplary only. In order to specifically deliver or transfect cells which are abnormally proliferating and spare non-dividing cells, it is preferable to utilize a retrovirus delivery system known to those of skill in the art. Since host DNA replication is required for retroviral DNA to integrate and the retrovirus will be unable to self replicate due to lack of the retrovirus genes needed for its life cycle, utilizing such a retroviral delivery system the present invention will target said antiproliferative elements to abnormally proliferating cells and will spare non-dividing normal cells from any intervention.

The mutant proteins of the present invention may be administered in any biologically effective carrier. The biologically effective carriers may include retroviruses, liposomes, and any other transfection mechanism capable of introducing foreign proteins into the genome of the cell. Such transfection mechanisms are known to those of skill in the art. The carrier may also include any agent or solvent with which the constructs of the present invention are compatible and which are non-toxic to the individuals or cells treated at the amounts administered.

Pathological cell proliferative conditions to be treated

There is a wide variety of pathological cancerous and noncancerous cell proliferative conditions for which the method of the present invention will provide therapeutic benefits. These pathological conditions may occur in almost all cell types capable of abnormal cell proliferation. Among the cell types which exhibit pathological or abnormal growth are (1) fibroblasts, (2) vascular endothelial cells and (3) epithelial cells. It can be seen from the above that the method of the present invention is useful in treating local or disseminated pathological conditions in all or almost all organ and tissue systems of the individual.

For instance, in the eye alone, the method of the present invention may be utilized to treat such a wide variety of pathologic disease states caused by abnormal proliferation of normal (benign) or malignant cells or tissues including, but not limited to, the following fibroproliferative, vasoproliferative and/or neoplastic diseases of the eye: retinopathy of prematurity, proliferative vitreoretinopathy, proliferative diabetic retinopathy, capillary hemangioma, choroidal neovascular nets, subretinal neovascular nets, senile macular degeneration due to subretinal, neovascularization, corneal neovascularization, macular pucker due to epiretinal membrane proliferation, adult cataracts due to nuclear sclerosis, fibrous ingrowth following trauma or surgery, optic nerve gliomas, angiomatosis retinae, neovascular glaucoma, cavernous hemangioma, rubeosis iridis, sickle cell proliferative retinopathy, epithelial downgrowth after eye surgery or injury, after-cataract membrane, papilloma, retinal neovascularization in thalassemia, subretinal neovascularization due to pseudoxanthoma elasticum, and neurofibromatosis type 1 and 11, retinoblastoma, uveal melanoma and pseudotumor of the orbit. Other benign cell proliferative diseases for which the present invention is useful include, but are not limited to, psoriasis, ichthyosis, papillomas, basal cell carcinomas, squamous cell carcinoma and Stevens-Johnson Syndrome.

In general, the present invention is applicable to all forms of cancer including but not limited to cancers in which the inactivation of the Rb gene and/or the p53 gene have been implicated such as osteosarcoma, soft tissue sarcomas, melanomas, fibrosacroma, retinoblastoma, carcinoma of the breast, bladder, cervix, lung, colon, ovary, kidney, pancreas, and prostate. Furthermore, the novel mutant p53 proteins may be used to induce apoptosis in various cells. Thus, the present invention also is directed to a method of inducing apoptosis comprising the step of administering a novel mutant p53 protein of the present invention.

In addition, the present invention provides a method of treating a tumor cell having a mutation of a cyclin protein, comprising the step of administering a novel mutant p53 protein of the present invention to a cell. Representative mutations, e.g., translocations, amplifications of cyclin D1, cyclin D2 or cyclin D3 may be treated with the novel mutant p53 proteins of the present invention.

EXAMPLE 1

A conformation determining domain conserved between pRb and p53

The present invention discloses a conserved homologous structural domain that controls the conformations of the two tumor suppressor gene products, Rb and p53, thus allowing the creation of mutants of these genes and methods for their use. Thus, the present invention provides an isolated DNA molecule, wherein said molecule is a mutated growth suppressor gene. In one preferred embodiment of the present invention, the mutated growth suppressor gene is a mutated Rb gene. In another preferred embodiment of the present invention, the mutated growth suppressor gene is a mutated P53 gene.

In an attempt to understand the interaction between pRb and its cellular targets, antibodies to the various hydrophilic regions of the Rb protein were raised. Since different regions of the Rb protein may be interacting with different proteins, it was necessary to raise antibodies to many different regions such that some of the antibodies would bring down the protein complex between the Rb protein and its targets without interfering with their interaction. Of a panel of polyclonal anti-Rb antibodies raised against synthetic peptides with sequences corresponding to various hydrophilic domains, two of them (Rb1-Ab 18 and Rb1-Ab20) consistently bring down, in addition to the Rb protein, a protein of molecular mass 53 kD (FIG. 1A, lanes 1, 2, 8 and 9). These two antibodies turned out to be raised against the same synthetic peptide, p5. The appearance of the 53 kD protein is specific for antisera raised against p5. Antisera against other regions, for example Rb1-Ab B (FIG. 1, lanes 4–5) and Rb1-Ab C (FIG. 1, lanes 6–7) did not immunoprecipitate the 53 kD protein although they can still recognize the Rb protein. Because of the similarity in the molecular mass of this protein and that of p53, it appears that this was the p53 protein itself. Immunoprecipitation of the cell lines with Pab122, a monoclonal antibody against p53 showed that the p53 indeed has the same exact molecular mass as that of the 53 kD protein (lane 10). Furthermore, if p53 was first removed from the cell lysate with Pab 122, neither Rb1-Ab 18, or Rb1-Ab20 can immunoprecipitate the 53 kD protein, although they still can precipitate the Rb protein (lane 11). To further verify that the 53 kD protein was indeed p53, immunoprecipitation was done on several cell lines which expressed no endogenenous p53 and/or Rb protein. In all cases (lanes 12–20) the antibody indeed can recognize the p53 protein in accordance with the status of the presence or absence of the p53 gene in these cell lines. Furthermore, the immunoprecipitation of p53 is independent of the presence or absence of the Rb protein, suggesting that a complex was not formed and that the p53 protein was recognized by the antibodies directly.

Figure 2A:
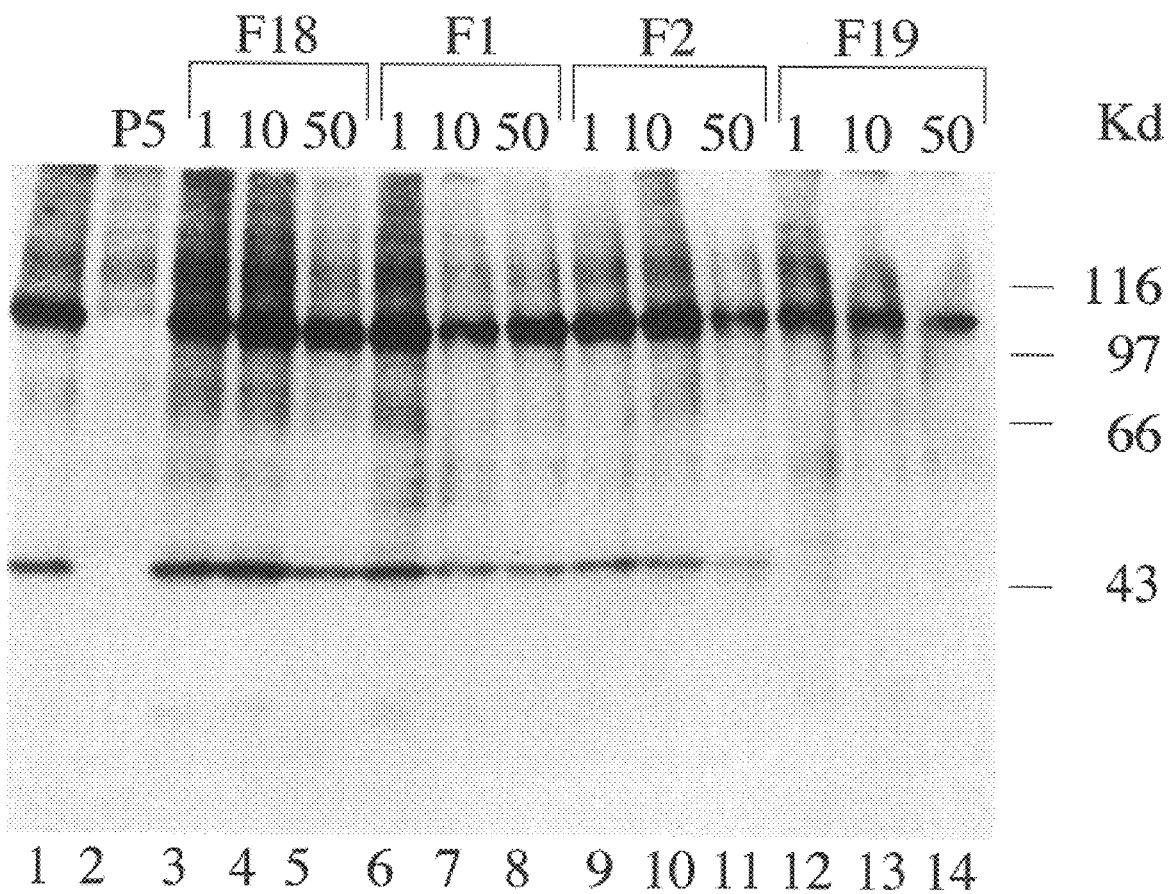
FIGS. 2A and B show the confirmation of the homology region between pRb and p53 immunoprecipitation of cellular protein using polyclonal anti-Rb antibodies RB1-Ab #18 and #20.

To definitively show that the P53 protein shares a common antigenic domain with the Rb protein, a search of the amino acid sequence of the p53 protein corresponding to the P5 region of the Rb protein was initiated. If the 3-dimensional structural information was retained in these two proteins and in the P5 peptide, there may be a corresponding region on the P53 protein. Furthermore, a peptide with this conserved antigenic domain should block the immunoprecipitation of P53 by RB1-Ab 18 or RB1-Ab 20. Immunoprecipitation of Rb and p53 proteins by Rb1-Ab18 (FIG. 2A) were performed in the presence of various amounts of these peptides. One such p53 peptide, F19, completely blocked the immunoprecipitation of p53 by Rb1-Ab18 at the lowest concentration (10 ug/ml) tested (FIG. 2A, lanes 12–14). This was also the same concentration of the Rb peptide p5 used to block the precipitation (lanes 1 and 2). In contrast, all other p53 peptides failed to block the immunoprecipitation of p53 by Rb1-Ab18, even at 50 to 100 times the concentration used (lanes 3–11).

The p5 and F19 region are not the only regions that show structural homology between the Rb and p53 proteins. At least two other regions were identified by visual and computer search. For comparison, the homology regions of Rb and p53 are shown in Table I.

TABLE I

Comparison of the homology regions between Rb and p53

| | (P1 region) | (67% homology) | |
|---|---|---|---|
| Rb | EINSALVLK | (184–192) | (SEQ ID NO:4) |
| P53 | ELNEALELK | (343–351) | (SEQ ID NO:5) |

| | (P3 region) | (67% homology) | |
|---|---|---|---|
| Rb | RRGONRSAR | (245–262) | (SEQ ID NO:6) |
| P53 | KKGOSTSRH | (372–380) | (SEQ ID NO:7) |

| | (P5 region) | (62% homology) | |
|---|---|---|---|
| Rb | KKLRFDIEG--SD | (873–886) | (SEQ ID NO:8) |
| P53 | KKLMFKTEGPDSD | (381–393) | (SEQ ID NO:9) |

Figure 2B:
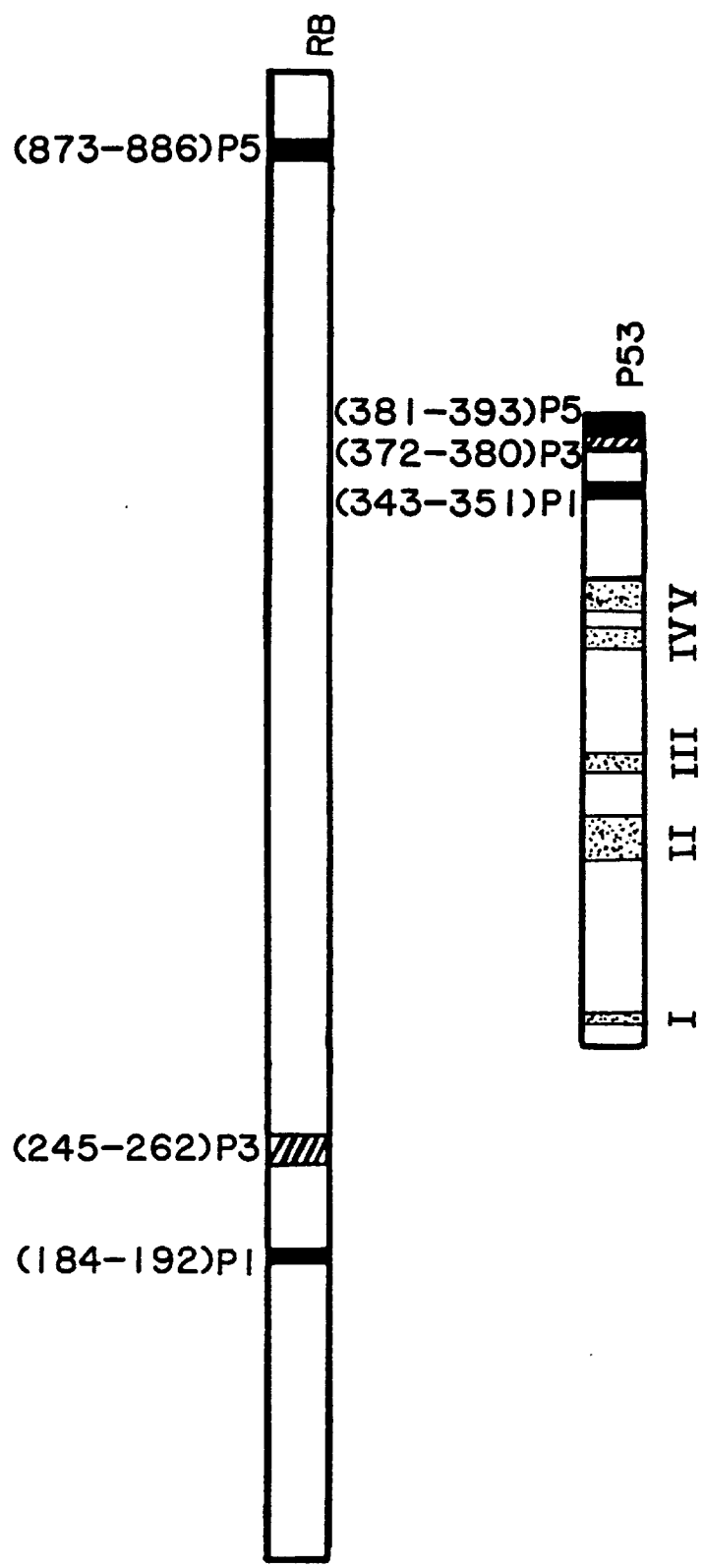

Although these regions may appear to be short, those amino acids that are homologous between pRb and p53 also are the most evolutionarily conserved ones in p53 (there is no data available for the sequence of Rb in different species). This high degree of homology between the two growth suppressor proteins suggest that these regions may have important functions. A schematic drawing of the positions of the homology regions on pRb and p53 is shown in FIG. 2B. In p53, all three regions are clustered in the C-terminus of the protein and in pRb regions 1 and 3 are clustered in the N-terminal half while the P5 region is at the C-terminal half. However, in both p53 and pRb these three regions are all located outside of the domains known to be important for the suppression function of the proteins. If these regions are not responsible for the physical interaction with their suppression targets, it may be that they are responsible for the regulation of the interaction process. Just as it is important to have active Rb and p53 proteins to suppress unwarranted cell growth, it is equally important to have a means to down-regulate their activities so that a cell may proliferate. The presence in these two growth suppressor gene products of the conserved domains may ensure their coordinated regulation. Indeed, as is shown below, these homology regions appear to form a domain which determines the conformations of the two proteins. Specifically, disruption of this domain by mutation at the conserved amino acids residues (underlined in Table I above) of any one of these three regions conferred upon the two proteins an active conformation. In contrast, mutations at the unconserved amino acids in these regions have no effect.

EXAMPLES 2

Figure 3:
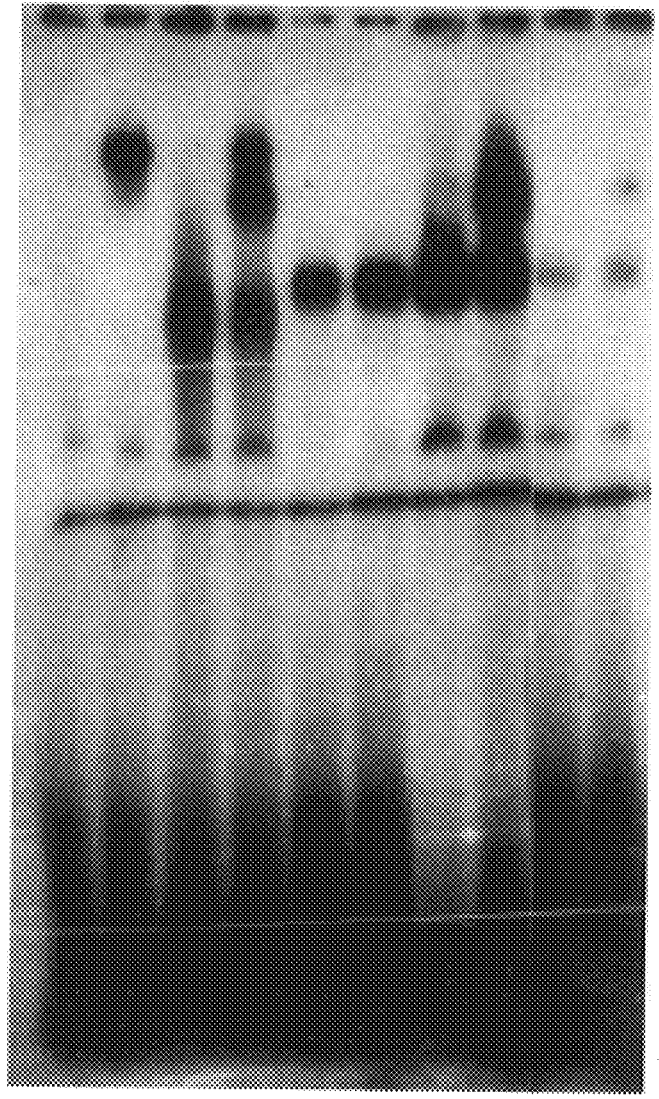
FIG. 3 shows the ability of the P1, P3, P5 mutant p53 proteins to bind specific DNA sequences in the absence of Pab421.
Figure 10:
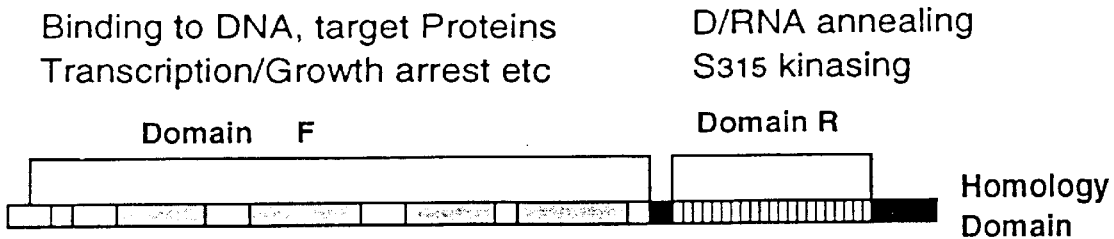
FIG. 10 shows a shematic diagram of both the wild type p53 protein showing the domain F and domain R and the mutant p53 protein showing the domain F and domain R.
Figure 10:
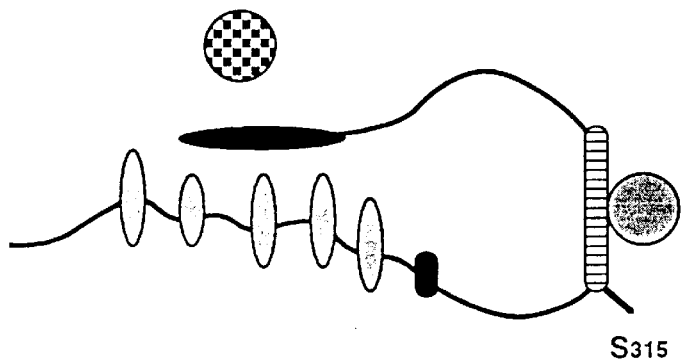
Figure 10:
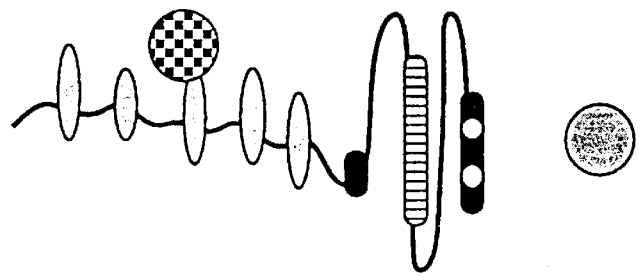

FIG. 10 shows a schematic representation of the conformations of the wildtype and the mutant p53. Two domains are described, domain F (function) and domain R (regulation). Domain F is the region of p53 containing the five domains conserved in different vertebrate species. Naturally occurring mutation at one of these five domains lead to the inactivation of the wildtype function of p53. The present invention shows that domain F is exposed in the Rb/p53 mutant but not in the wildtype with important functional consequence. Domain R represents the C-terminus motif that is just outside of the domain needed for the binding of p53 to specific DNA sequences. This domain contains the Rb/p53 homology domain p1, p3, p5. Domain R is hidden in the Rb/p53 mutant but not in the wildtype with important functional consequences as detailed by the present invention. FIG. 10 shows a shematic diagram of both the wild type p53 protein showing the domain F and domain R and the mutant p53 protein showing the domain F and domain R. In FIG. 3, the synthetic mutant p53 was shown to bind to specific DNA sequences, suggesting that the synthetic mutant p53 is assuming a conformation different from that of the wildtype. Thus, the DNA binding domain of the synthetic mutant p53 may also be able to bind to other proteins that can to bind to domain F.

EXAMPLE 3

P1, P3, P5 regions control p53 conformation and DNA binding ability

The ability of p53 to activate transcription is tightly related to its ability to bind DNA. Mutant p53 found in cancer cell lines are unable to bind to DNA and unable to activate transcription. The P53 protein is capable of binding to specific DNA sequence in the presence of the antibody Pab421. A close inspection of the epitope of the Pab421 revealed that it overlaps with the P3 region. The epitope recognized by Pab421(see FIG. 3) is the last four amino acid residues in the P3region. It appears that blocking this entire P3 region with an antibody (Pab421) sufficiently changed the conformation of the protein allowing the p53 protein to bind with a specific DNA sequence. The DNA binding assay therefore provided a convenient means of testing the role of the P3and the other homologous regions P1, and P5 in the control of the conformation of the P53 protein. As is shown in FIG. 3, while the wild type p53 was unable to bind to its specific DNA sequence (lane 1), it does bind in the presence of the antibody Pab421 (lane 2). When the conserved amino acids of either the P1 (lane 3), P3 (lanes 5 and 7) or P5 (lane 9) regions of p53 was mutated, the resulting p53 mutant proteins were able to bind to DNA even in the absence of Pab421. The resulting complex was supershifted upon binding to Pab421 (lanes 4, 8, and 10 for P1, P3, P5 respectively). This supershift is an indication that the P3 region in these mutants are still capable of binding to the antibodies and that the ability of the mutants to bind DNA in the absence of Pab421 was not due to mutation at the P3 region. In fact, binding of the antibodies Pab1801 outside of these C-terminal domain also allowed a supershift of the complex. The mutant used in lanes 7 and 8 was mutated at the first 4 amino acid residue of the P3 region and that apparently does not affect the binding of Pab421 to the protein. The mutant used in lanes 5 and 6 was mutated at the conserved amino acids of the last 4 residues in the P3 region and that abolished the binding of Pab421 to the protein. Mutation at the unconserved amino acids show no effect, the proteins behaved essentially like the wild type. Thus, the conformation of the mutant p53 proteins is switched to the active form when the homology regions are destroyed by mutation.

Examples 3–7 of the present invention demonstrate (1) the ability of the mutant p53 to bind specific DNA sequences; (2) the ability of the mutant p53 to bind to cyclin D1, D2 and D3; (3) the ability of the mutant p53 to resist phosphorylation by the cyclin A/cdk2 kinase at serine residue 315; (4) the ability of the mutant p53 to activate transcription in vivo and (5) the ability of the synthetic mutant p53 to induce apoptosis of tumor cells when used in conjunction with the chemotherapeutic agent, cisplatin.

EXAMPLE 4

Figure 11:
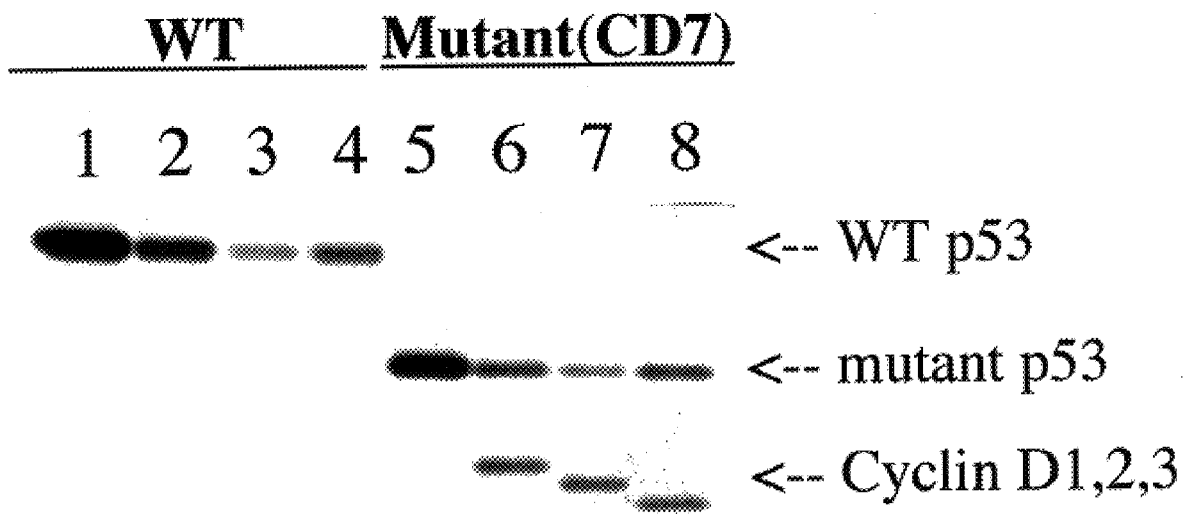
FIG. 11 shows that the mutant p53 protein is able to bind specific DNA sequences.

The present invention shows that p53 is able to bind to cyclin D1, D2 and D3. The deregulated expression of cyclin D is related to the development of various tumors including leukemia and mammary tumors. To show the binding of p53 to cyclin D, the corresponding recombinant baculoviruses were created and co-infected into sf9 cells. The co-precipitation is described in FIG. 11 which shows that the mutant p53 protein is able to bind specific DNA sequences. The p53 protein was precipitated using a monoclonal antibody PAb 1801. As is shown in the FIG. 11, wildtype p53 (lane 1) was unable to bind to either of the three cyclin Ds when they were coexpressed in vivo in infected sf9 cells (lanes 2, 3, 4). In contrast, the mutant form of p53 in which the p3 and p5 regions were deleted (lane 5) was able to bind to cyclin D1 (lane 2), D2 (lane 3), and D3 (lane 4). Thus, the mutation of the Rb/p53 homology regions resulted in the exposure of the functional domain of p53 such that the p53 protein was able to interact with its binding target DNA and proteins. The invention also shows that one such protein was the protooncogene products cyclin D1, 2 and 3, the deregulated expression is important for tumorigenesis.

EXAMPLE 5

Figure 12A:
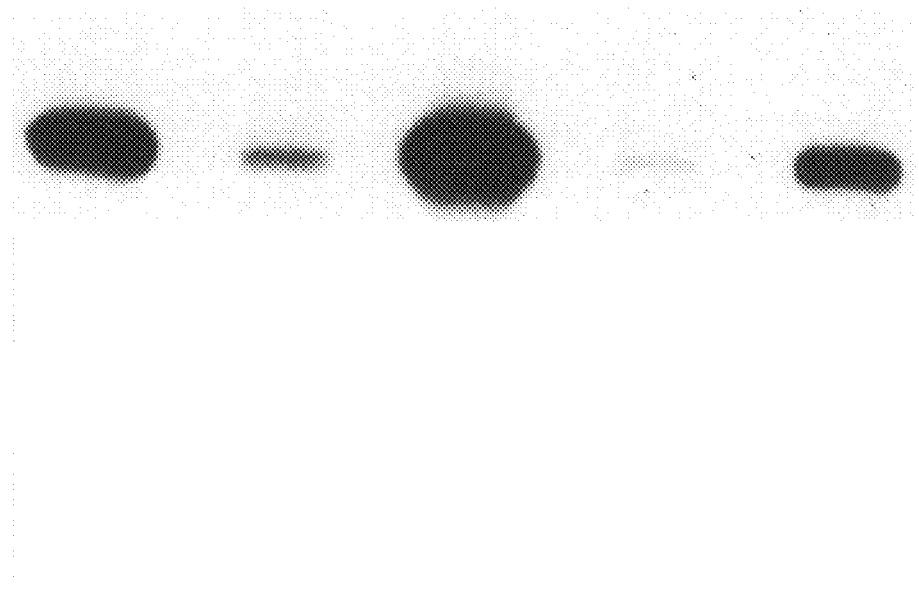
FIGS. 12A and B show that the homology regions control the exposure of the C-terminus of p53 so that specific sites are not phosphorylated.
Figure 12B:
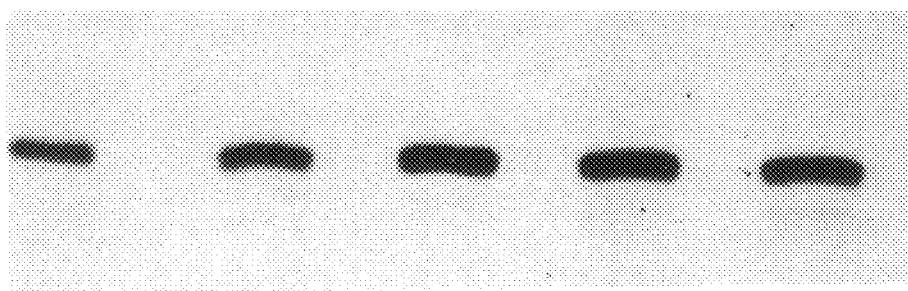

In addition to the activation (exposure) of the functional domain of p53, the conformational changes brought about by the mutation of the Rb/p53 region also resulted in specific change in the conformation of domain R in the C-terminus. Specifically, the serine residue 315 was not phosphorylated by any of the cyclin-dependent kinases as the wildtype. FIG. 12 shows shows that the homology regions control the exposure of the C-terminus of p53 so that specific sites are not phosphorylated.

p53 proteins were expressed in bacteria. An aliquot of the bacteria was labeled with $^{35}$S-cysteine and methionine for quantitation. Equal amount of purified p53 (FIG. 12B) were mixed with cyclin A: cdk 2 in a phosphorylation buffer containing $^{32}$P-ATP. The phosphorylation reactions were carried out at room temperature for 30 minutes. The p53 proteins were then precipitated with PAb1801. As can be seen in FIG. 12A, p53 was heavily phosphorylated whereas the synthetic mutant P53 mutated at the conserved aminoacid residues in domain P3(lane 3C) or P5 (lane 5C) were not phosphorylated, if at all. In contrast, mutation at the unconserved amino acid residues even within the P3 (3U) or the P5 (5U) regions had no effect on the phosphorylation of the protein. 2-dimentional mapping of the phospho-peptides confirmed that serine 315 is the predominant residue that is phosphorylated.

EXAMPLE 6

Figure 13A:
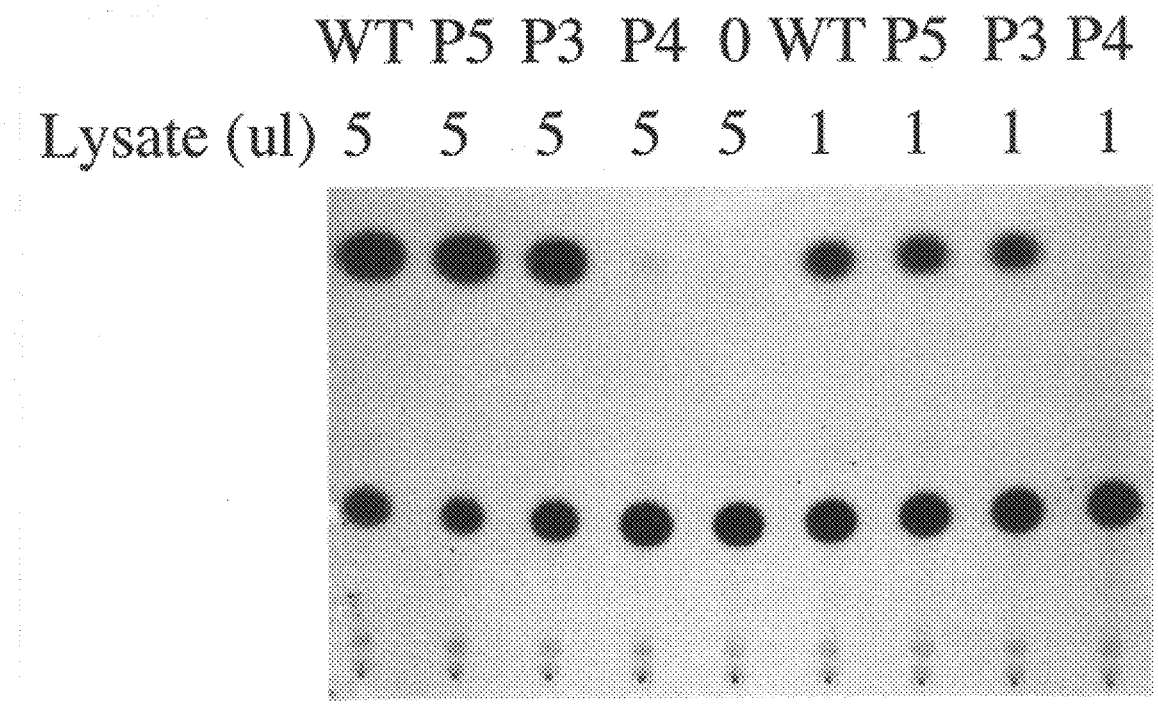
FIGS. 13A and B show that the homology region mutants of p53 are transcriptionally active in vivo.
Figure 13B:
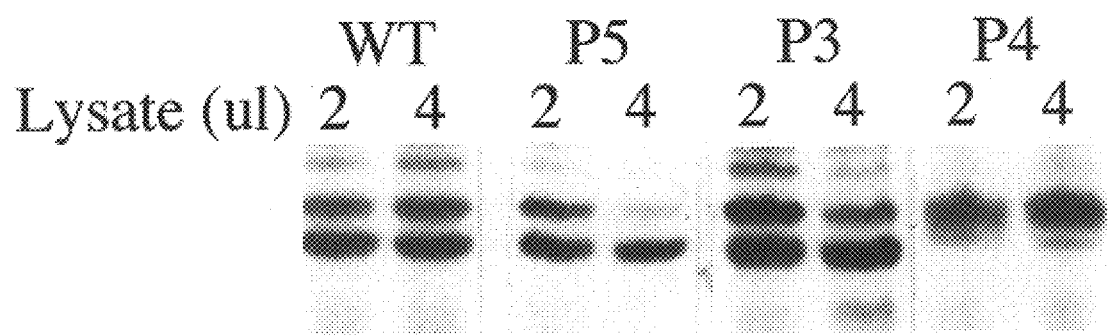
FIG. 13B demonstrates that equal amount of proteins were used for all the p53 constructs.

To demonstrate the functional properties of the homology region mutants, the human lung carcinoma cell line H358 which lacks endogenous p53 proteins was cotransfected with the p53 mutants and a reporter construct in which the CAT gene was under the control of a p53 CON. sequence containing a p53 consensus binding site. FIG. 13 shows that the homology region mutants of p53 are transcriptionally active in vivo. As is shown in FIG. 13A, p53 mutants of the P3 or P5 homology region at the conserved aminoacids was active in promoting transcription from a promoter with a p53 binding site and the amount of transcriptional activation by the mutants was equal, to or slightly higher than that of the wildtype. In contrast, the p4 mutant (which was mutated in the fifth conserved functional domain) abolished the ability of p53 to bind cyclin D or DNA and was totally defective in promoting transcription. In the middle of FIG. 13A, lane 0 represents the control in which only the vector without p53 inset was used. As expected, no transcription promotion can be detected). Equal amount of proteins were used for all the p53 constructs as demonstrated in FIG. 13B.

EXAMPLE 7

Figure 14A:
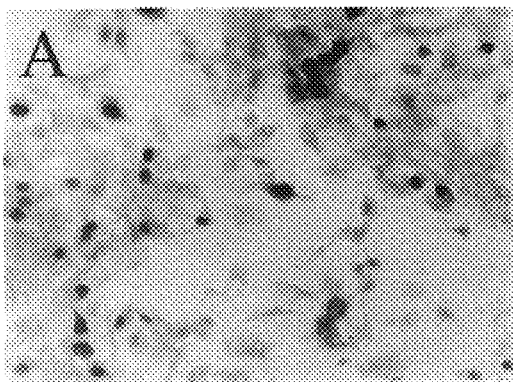
FIGS. 14A through F show that the synthetic p53 mutant induces apoptosis in the lung carcinoma cell line, H358.
Figure 14B:
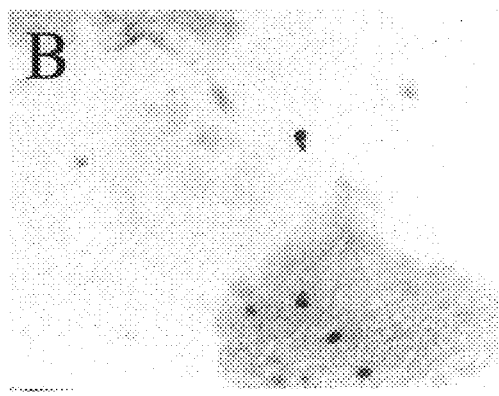
Figure 14C:
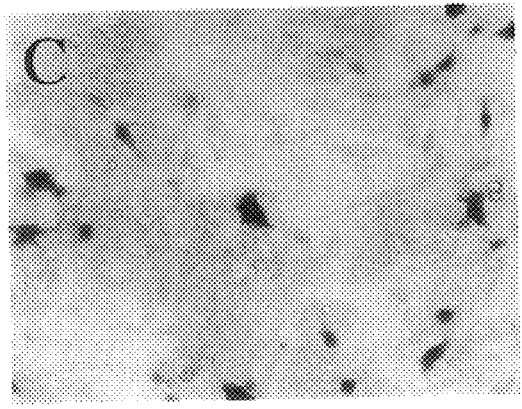
Figure 14D:
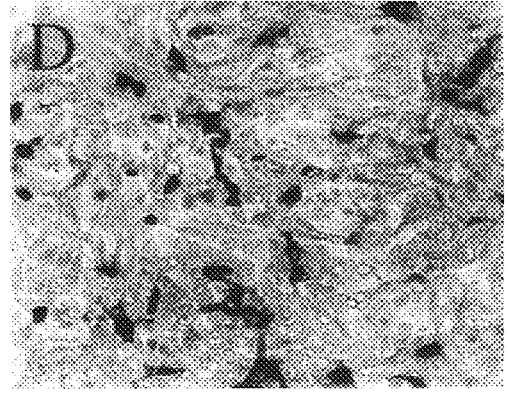
Figure 14E:
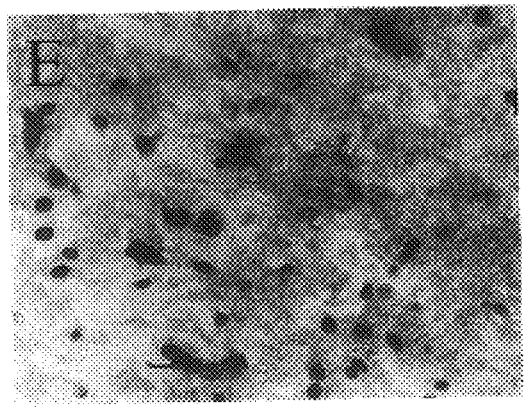
Figure 14F:
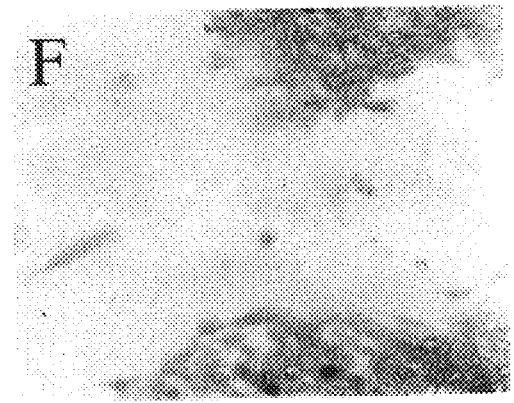

The introduction of a wildtype p53 has been shown to be effective in the induction of apoptosis of tumor cells when chemotherapeutic agent treatment alone failed to stop tumor growth. To show that the synthetic p53 mutant induced apoptosis, the lung carcinoma cell line H358 which is devoid of endogenous p53 protein due to an inactivating mutation was used. As a comparison, a batch of the same cell line was transfected with either the wildtype or the P4 mutant (which was shown to be inactive by several criteria). FIG. 14 shows that the synthetic p53 mutant induces apoptosis in the lung carcinoma cell line, H358. As is shown in FIGS. 14A, 14C, and 14E, approximately 5% of the H358 cells transfected with wildtype, P4 or P5 mutants respectively showed expression of the p53 proteins in the nucleus by immunostaining with the anti-p53 monoclonal antibody PAb122. (Compare the dark staining of the cell nuclei and the lack of staining in the surrounding cells). After the cells were treated with the chemotherapeutic agent c-DDP (cisplatin) for two weeks, most of the cells that expressed wildtype (FIG. 14B) or p5 mutant p53 (FIG. 14F) underwent apoptosis and disintegrated. In contrast, cells expressing the p4 inactive mutant p53 (FIG. 14D) continued to persist and indeed proliferated to a greater number than before treatment. Thus, the present invention demonstrated that the p5 mutant p53 induced apoptosis in conjunction with chemotherapeutic treatment.

EXAMPLE 8

Thus, the present invention demonstrates that the p53/pRb homology regions (P1, P3 and P5) control the conformations of the p53 protein in two different ways simultaneously. First, the functional domain (domain F) which is necessary for cell growth suppression and induction of apotosis, is exposed when the Rb/p53 homology regions in the C-terminus are modified or mutated. The exposure of the functionally important central region of these mutant p53 proteins is shown by their enhanced ability to bind to specific proteins and DNA sequences when compared to the wildtype protein. Secondly, the mutation of the homology regions also brought about conformational changes at the C-terminal regions. That is, domain R became hidden such that the ability of p53 to be phosphorylated at serine #315 is abolished. In addition, exposure of the C-terminal domains needed for double stranded DNA/RNA annealing activity is controlled by the P3 region, since blocking the P3 region with PAb421 allows translation of the p53 mRNA. This annealing activity prevents newly synthesized p53 mRNA from being translated. Therefore, mutations at any of the P1, P3 or P5 regions in the conserved amino acids resulted in a p53 conformation in which various activities known to be important to the growth suppressor function of the proteins are unmasked. The conformational change was not specific for any one particular effect.

EXAMPLE 9

Alteration in the control of the phosphorylation of Rb proteins mutated at the homology region There are several ways to distinguish between the active and inactive conformations of the pRb protein. Active Rb protein is underphosphorylated and can suppress the growth of the cell. Inactive Rb protein is heavily phosphorylated. If the homology domain affects the active and inactive conformation of pRb, mutation at the P1, P3, P5 regions should affect the ability of the protein to suppress cell growth and its phosphorylation accordingly. The P1, P3, and P5 regions of pRb were separately mutated at the conserved amino acid residues and the ability of the mutants to suppress cell growth examined. All mutants were able to suppress the growth of the transfected cells. The ability of the Rb mutant m 89-0, which is mutated at the conserved amino acid residues at the P5 region, to suppress the growth of normal and cancer cells is given in two Examples below. Since the activity of pRb is regulated by phosphorylation, if the conserved region is for the maintenance of pRb in an inactive conformation, mutation of the P5 region should have an inhibitory effect on the phosphorylation of the mutant pRb such that the protein is active.

There are cell lines which are devoid of pRb expression due to mutation of both alleles of RB-1 and these cell lines have also incurred other mutations which render them resistant to the suppression effect of a transfected Rb gene. The cervical carcinoma cell line C33A and a subpopulation of the Saos-2 are two such cell lines. These cell lines therefore would allow the mutant proteins to be expressed and the cells remain viable, allowing the extraction of abundant amounts of the protein for examination of the phosphorylation status. The P5 mutant HuAcPr-1-neo-P5 C, mutated at the conserved amino acid residues at the P5 region, was therefore transfected into these cells and stable cell lines were obtained by single cell purification. The phosphorylation patterns of the mutant pRb isolated from the purified mutant cell line Saos-2#89 was compared to that of the wild type pRb extracted from the wildtype Rb transfected and purified cell line Saos-2#84. Immunoprecipitation of pRb from S phase Saos-2#84 (wildtype) and Saos-2#89 (mutant) showed that the wildtype pRb was heavily phosphorylated whereas the mutant pRb was underphosphorylated. This suggests that the P5 mutant pRb remains in the active conformation even when the cells were in the S phase. Thus, the P5 mutant assumes a conformation which is resistant to phosphorylation at particular sites. It should be noted that the protein was still phosphorylated at other functionally unimportant sites.

Figure 4A:
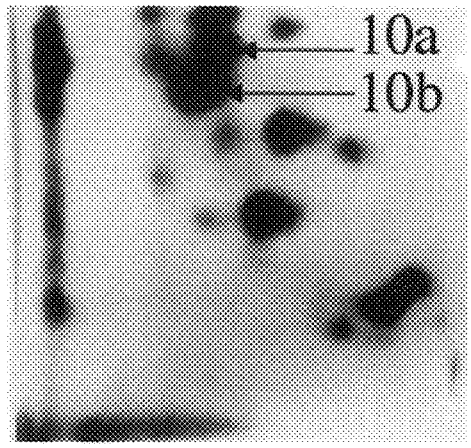
FIGS. 4A through B shows the two dimensional mapping analysis of the phosphorylation pattern of mutant Rb proteins as compared to those of the wildtype, (A) in vivo labelled proteins (B) in vitro labelled proteins.
Figure 4A:
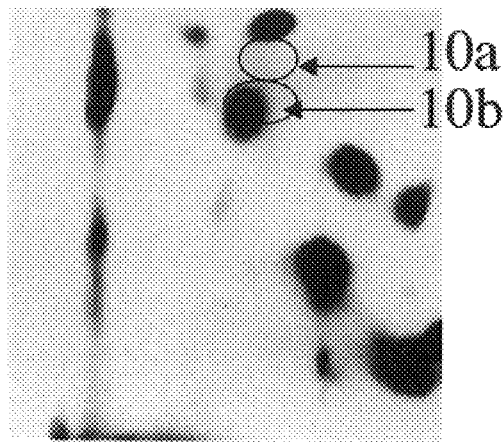
Figure 4B:
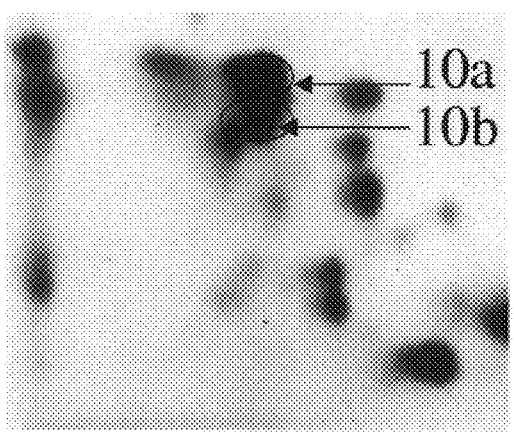
Figure 4B:
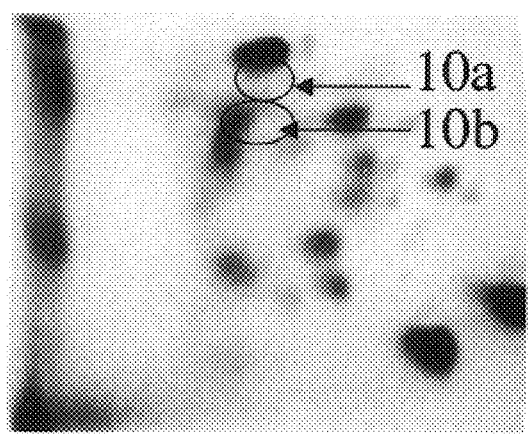

Since one-dimensional analysis by SDS-PAGE only revealed that the protein was underphosphorylated but not the nature of the underphosphorylation, two-dimensional phosphopeptide analyses of the $^{32}$P-labelled pRb using two different proteases, trypsin and chymotrypsin, was performed. A comparison of the 2-Dimensional maps revealed that there are 2 sites, S10a and S10b, that are consistently unphosphorylated in the mutant as compare to the wild type (FIG. 4A). To show that the difference in the phosphorylation pattern was due to an intrinsic difference in the conformation of the proteins instead of variation in in vivo enzyme specificity, the in vitro phosphorylation patterns of the proteins were compared. The wildtype and mutant pRb were phosphorylated using a kinase preparation that consist of cyclin associated kinases. The in vitro labelling was dependent on the cyclin associated kinase as antibodies against the kinase blocked the phosphorylation. The in vitro phosphorylated pRb were analyzed by 2-Dimensional peptide mapping and as shown in FIG. 4B, the same phosphorylation sites were not used in the mutant. Therefore, even with the supply of abundant amounts of enzymes and optimum phosphorylation conditions in which the wildtype pRB was phosphorylated to completion, the mutant pRb was completely resistant to the phosphorylation sites S10a and 10b. The variation in the phosphorylation of S10a and S10b is therefore due to an intrinsic difference in the conformation of the wildtype and the mutant proteins instead of variation in in vivo enzyme specificity.

EXAMPLE 10

Figure 5A:
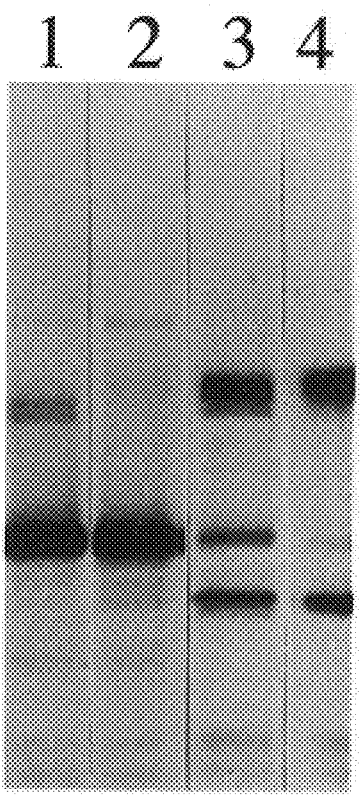
FIGS. 5A and B show the binding of the retinoblastoma protein to the SV40 large T antigen and the dissociation of the complex by phosphorylation.
Figure 5B:
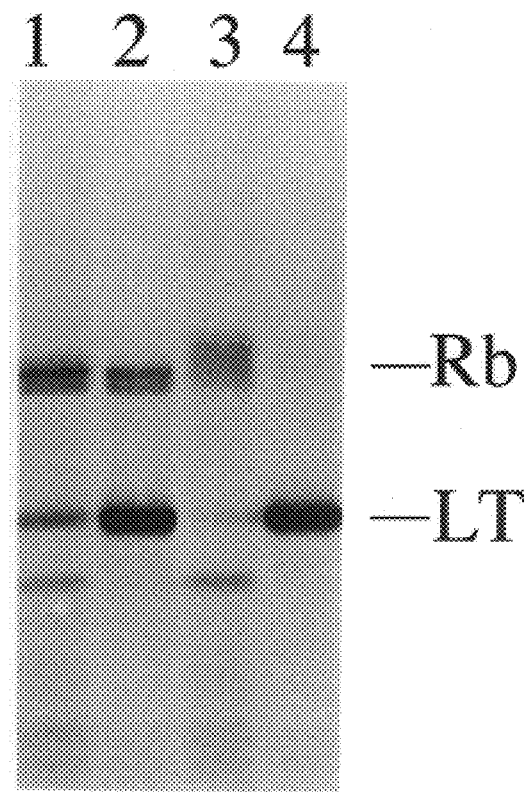

Rb proteins mutated at the homology region are active
Correlation of phosphorylation at S10a and S10b with pRb activity The data provided below demonstrates that the variation in the phosphorylation at S10a and S10b correlates with the ability of pRb to bind SV40 large T antigen. For in vitro phosphorylation studies, Rb protein was isolated from sf9 cells infected with a recombinant Rb-Baculovirus in which the polyhedrin gene was partially replaced with the Rb gene. It was noticed that, under high infection titer conditions, although the majority of the Rb protein extracted was rendered incapable of binding to the SV40 large T by phosphorylation, a small proportion of Rb protein that remained bound to large T. This binding is shown in FIG. 5. The Rb protein and the SV 40 large T were obtained from $^{35}$S-labeled SF9 cells infected with the corresponding bacculoviruses and kinased in vitro. Lane 1 shows that the Rb proteins extracted consisted of underphosphorylated as well as hyperphosphorylated forms and some of the proteins bound to large T. Large T could bind only the underphosphorylated form of the RB protein (lane 2 and lane 3). Phosphorylation of this large T:Rb complex with different amounts of Rb kinase (lanes 3 through 6) released the majority of the Rb protein from the large T. This form of the RB proteins can be termed RB-E (E=exposed critical site). However, approximately 20–30% of the Rb protein (termed RB-H) (H=hidden critical site) remained tightly bound to large T and the whole complex could be brought down by anti-large T antibody. Most importantly, although increasing amount of the Rb kinase could phosphorylate the Rb protein to its slowest migrating form (compare lane 4 through 6 and lanes 8 through 10), the hyperphosphorylated Rb protein remained bound to the large T. That the precipitation of these Rb proteins was not due to nonspecific absorption to the protein A agarose is shown by comparison of lane 6 with lane 2. Approximately 70% of the Rb protein was released from the large T. This released Rb protein was not due to a nonspecific degradation of the protein as shown by the fact that if the reaction was precipitated with anti-Rb antibodies, all of the Rb proteins were accounted for (as shown in lanes 8, 9 and 10). The ability of the various forms of Rb protein to bind to large T is also shown in lanes 8, 9 and 10, in which a smaller amount of large T was brought down by the Rb protein.

Figure 6:
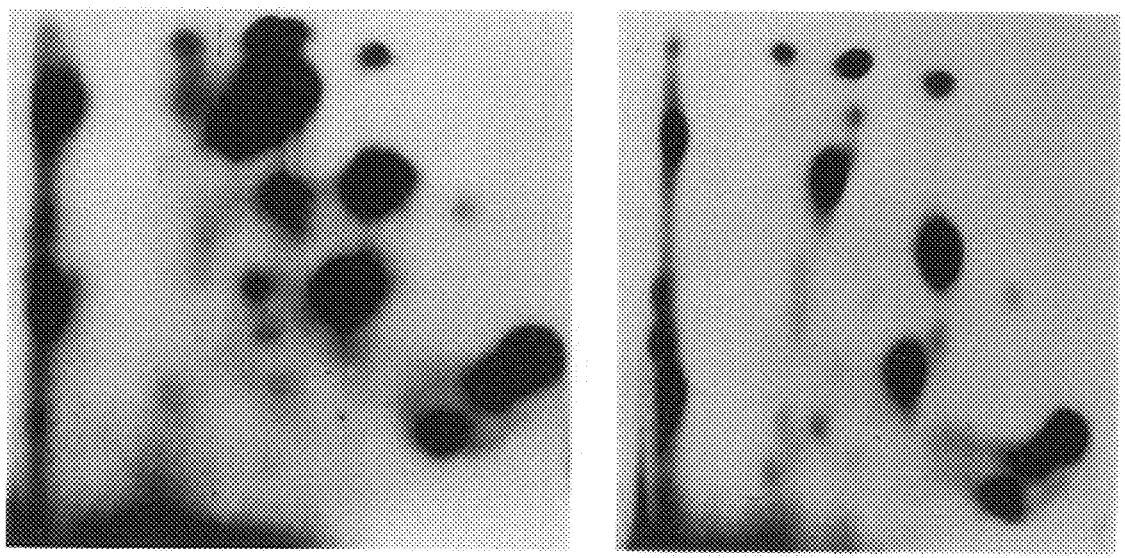
FIG. 6 shows the two dimensional mapping analysis of two different forms of phosphorylated retinoblastoma protein (those that are bound by SV40 large T and those that are not).

These results are consistent with the presence of two classes of phosphorylation sites on the Rb protein, with one being critical for the inactivation of the Rb protein so that it cannot bind to large T, whereas the others can be phosphorylated without affecting the binding. There are 17 potential phosphorylation sites (S/TPXX) for the Rb kinase complex. To demonstrate that the phosphorylation sites are important for the inactivation of the Rb protein, a 2-D mapping analysis was performed on the Rb protein that remains bound to the SV40 large T (RB-H) and on those that are free from the SV40 large T after phosphorylation (RB-E). There must be a difference in the phosphorylation sites between these two forms of Rb protein if the disassociation of Rb from large T is a result of phosphorylation. As is shown in FIG. 6, S10a and S10b were found not to be phosphorylated in the pRb that remain bound to the large T protein.

Mutation at the conserved amino acids at the P5 region renders the protein an active conformation. The phosphorylation at S10a and S10b is a function of the cell cycle and correlates with the ability of the cell to proliferate.

EXAMPLE 11

Phosphorylation at S10a and S10b of pRb and cell growth

The data provided below demonstrates that the variation in the phosphorylation at S10a and S10b is regulated in a cell cycle dependent manner. It is well documented that exposure of cells, normal or cancerous, to TGF-β frequently lead to growth arrest. A role of pRb in the suppression of cell growth has previously been described. To show the role of TGF-β on the phosphorylation of pRb, the breast carcinoma cell line MDAMB231 which can be growth arrested by treatment with TGF-β was employed. The proliferation status of the cells were monitored by tritiated thymidine uptake and the phosphorylation pattern of the $^{32}$P-labelled pRb analyzed by 2-Dimensional peptide mapping. Significantly, the pRb from cells growth arrested by TGF-β were not phosphorylated at S10a and S10b (FIG. 7). However, when the cells were released from the TGF-β, S10a and S10b were again phosphorylated. Thus, the pRb protein which is active in growth arrested cells were not phosphorylated at S10a and S10b. That this reversible phosphorylation was not just specific to the growth suppression effect of TGF-β was shown by the fact that similar phosphorylation pattern of S10a and S10b was also found in pRb isolated from cells growth arrested by deprivation of serum. Upon refeeding with either serum or growth factors, S10a and S10b was once again phosphorylated. In addition, S10a and S10b was not phosphorylated in pRb isolated from cells growth arrested by retinoic acid. Therefore, the functionally critical S10a and S10b sites in the pRb protein can undergo reversible phosphorylation under different growth conditions.

EXAMPLE 12

Mutants of the Rb gene and the p53 gene

Thus, for both pRb and p53, mutation of the homology region resulted in the proteins assuming conformations that render them active. Examples of the conformationally active mutants of Rb and p53, and their uses in suppression of cell growth, are given below. For the Rb protein, two classes of mutants are described, (1) mutants in the regulatory or homology region, and (2) mutants in the phosphorylation sites. For the p53 protein, mutants of the homology regions are described.

Phosphoamino acid analysis of hyperphosphorylated Rb proteins revealed that the amino acids serine and threonine are phosphorylated. There are 79 serine and 55 threonine residues in the Rb protein. Of these, 17 are found in the motif (S/TPXX), a potential phosphorylation site for the cdc2 kinase. The cdc2 kinase, and related kinases, are known to be able to phosphorylate the Rb protein.

There appear to be two classes of phosphorylation sites on the Rb protein, with one being critical for the inactivation of the Rb protein so that it cannot bind to large T, whereas the others can be phosphorylated without affecting the binding. Because there are at least 17 potential phosphorylation sites (S/TPXX) for the Rb kinase complex, several may be important for the inactivation of the Rb protein. These 17 phosphorylation sites are T005, S230, S249, T252, T356, T373, S567, S608, S612, T773, S780, S788, S795, S807, S811, T821, T826, where T and S denotes threonine and serine, respectively, and the number that follows denote the residue number of the amino acid in the Rb protein.

The mutated retinoblastoma gene is preferably mutated by one of two different ways, both of which affect the ability of the protein to be phosphorylated. First, the gene may be mutated by changing amino acids in conserved homology regions of the Rb gene. Preferably, the conserved homology region of the Rb gene is selected from the group consisting of P1, P3, and P5, as described herein. Representative examples of mutated Rb genes that encodes for a mutated Rb protein is shown in Seq. ID. No. 1 and 2. A person having ordinary skill in this art, with the knowledge of the importance of the conserved homology domains to the phosphorylation of the protein, could easily construct other mutated Rb genes that encode for other desirable mutated Rb proteins.

A second way of preventing the phosphorylation and thus inactivation of the Rb protein is when said gene is mutated by changing amino acids in the phosphorylation sites. Preferably, the phosphorylation sites are selected from the group consisting of T005, S230, S249, T252, T373, S567, S608, S612, T773, S780, S788, S795, S807, S811, T821 and T826. In the abbreviations for the phosphorylation sites above, S refers to serine, T refers to threonine, and the number refers to the placement of the amino acid in the sequence of the Rb protein. For the phosphorylation mutants disclosed herein, each of the threonine or serine residues was mutated into alanine in individual plasmids. As stated before, there are at least 2 classes of phosphorylation sites, one of which is the functionally important for the inactivation of pRb. Therefore one or more of the mutants created above should negate the phosphorylation of the mutant pRb and prevent its inactivation.

In other embodiments of the present invention, there are also provided plasmids comprising the DNA encoding for mutated Rb proteins. In addition, also provided is a plasmid adapted for expression in a recombinant cell comprising the DNA encoding for a mutated Rb protein of Seq. ID. No. 1 and regulatory elements necessary for expression of the cDNA in the cell and a plasmid adapted for expression in a recombinant cell comprising the DNA encoding for a mutated Rb protein of Seq. ID. No. 2 and regulatory elements necessary for expression of the cDNA in the cell.

EXAMPLE 12

Mutants of the p53 gene

In another embodiment of the present invention, the mutated growth suppressor gene is a mutated p53 gene. Preferably, the p53 gene is mutated by changing amino acids in conserved homology regions of the p53 gene (underlined in Table I above). Similarly, the conserved homology region of the p53 gene is selected from the group consisting of P1, P3 and P5. Mutants can be consisting of mutations at either P1,P3, or P5, singularly or in any combinations (including mutations of all three regions). In addition, mutants in which the C-terminal amino acid residues 295–393 were deleted were still active in binding to the specific DNA sequence.

EXAMPLE 13
Use of pRb and p53 mutants for cell growth suppression

The present invention also discloses novel transfected cells, e.g., the transfected cell comprising the isolated DNA molecule of claim 1 which encodes a mutated Rb protein. Also provided by the present invention are stably transfected cells expressing a mutated Rb gene encoding for a mutated Rb protein. Preferably, the transfected cells of present invention contain the mutated Rb gene comprising a nucleic acid sequence encoding for a mutated Rb protein shown in Seq. ID No. 1 or Seq. ID No. 2. In addition, the present invention also provides a stably transfected cell expressing a mutated p53 gene encoding for a mutated p53 protein.

The present invention also provides a method for the treatment of pathological cell proliferative diseases comprising administration to a non-cancerous proliferating cell of the DNA molecule of a mutated growth suppressor gene. The molecule administered, in one embodiment, is a mutated Rb or p53 gene. The gene is mutated by changing amino acids in conserved homology regions of the Rb gene or said gene is mutated by changing amino acids in phosphorylation sites. The conserved homology regions and the phosphorylation sites are the same as described above.

Generally, this method may be used to treat any cell proliferative disease. Representative examples of non-cancerous cell proliferative disease include psoriasis, benign proliferative skin diseases, ichthyosis, papilloma, basal cell carcinoma, squamous cell carcinoma, fibroproliferative diseases, vasoproliferative diseases and dermatoproliferative diseases.

The present invention also provides a method of treating malignant cell diseases in individuals comprising administration into a proliferating cancer cell of a DNA molecule of a mutated Rb or p53 gene. These mutated genes are constructed as described above.

Generally, the method of treating malignant cell diseases is similar to the treatment of non-cancerous cell proliferative diseases. Representative examples of diseases caused by proliferating cancer cells, include but not limited to, osteosarcoma, fibrosacroma, retinoblastoma, carcinoma of the breast, bladder, cervix, lung, colon, ovary, kidney, pancreas, and prostate.

According to the method of the present invention, one can manipulate the cellular proliferative process by the introduction of a mutant RB or p53 protein to prevent or inhibit abnormal proliferation in a wide variety of cell proliferative diseases. The manipulation of the proliferative process may be accomplished by introducing into a target proliferating cell a DNA construct which encodes a mutant RB or p53 protein element.

The present invention also provides a method for the treatment of focal cell proliferative diseases comprising administration of the mutated Rb or p53 gene to proliferating cells. Generally, the proliferating cell may be the cause of such representative diseases as fibroproliferative, vaso-proliferative and neoplastic diseases in the eye.

In another embodiment, the phosphorylation site of the Rb gene is mutagenized before introduction into a cell. There are 17 potential phosphorylation sites on the Rb protein. Mutation of the serine or threonine coding sequences in the Rb cDNA into alanine or valine or others would therefore lead to the production of a permanently active Rb protein which cannot be inactivated by phosphorylation. That is, the host cell will not be able to inactivate the Rb protein by phosphorylation. Introduction of such a mutated Rb gene into a cell will therefore lead to growth arrest. All these mutants have been subcloned in the human β-actin promoter vector. For subcloning of the Rb cDNA, the entire open reading frame was ligated to a synthetic linker containing the BamH1 site at the 5' end and a synthetic linker containing AATAAA and a BamH1 site at the 3' end. The resulting BamH1 fragment was subcloned into the BamH1 site of the vector and the clone with the correct orientation selected.

EXAMPLE 14
Preparation of the p5 mutants m89-0 and m88-0

To create the m89-0 mutant, a pair of DNA oligonucleotide primers (Pm1 and QM1) containing the region 'P5' to be mutated and a pair of oligonucleotides flanking the region 'P5' (P3 and Q3) were synthesized using the AB 1 PCR-mate oligonucleotide synthesizer according to manufacturer instruction. Using the wild type Rb cDNA as the template, 40 cycles of polymerase chain reactions (PCR) were performed with the primers P3 and Qm1. In a second tube, 40 cycles of polymerase chain reactions were performed with the primers Pm1 and Q3. After the completion of the reaction, a small aliquot of the reaction product was taken from the first tube and 80 cycles of PCR were performed in the presence of excess P3 primer. Similarly, 80 cycles of PCR were performed in the presence of excess Q3 primer in the second tube. The predominately single strand reaction products from these two tubes were then combined and allowed to primer extend for 20 cycles. The resulting double stranded product, now containing the mutated P5 region were subcloned into the Rb expression plasmid HuBAcpr-1-neo-PQ (m89-0) at the Mlu 1 and Hind 3 sites. The resulting plasmid has a mutated P5 region shown below with the mutated amino acids underlined. K870 and H890 refer to the lysine and histidine amino acid residues at position 870 and 890 respectively in the Rb protein. m88-0 was created similarly.

Wildtype Rb:- $K_{870}$PLKKLRFDIEGSDEADGSKH$_{890}$ (SEQ ID NO:3)

Mutant m89-0 Rb:- $K_{870}$PLKKLRFDIEASAEVDASIH$_{890}$ (SEQ ID NO:2)

Mutant m88-0 Rb:- $K_{870}$LLIKPRYDTEGSDEADGSKH$_{890}$ (SEQ ID NO:1)

EXAMPLE 15
Effect of Transfected Plasmids on the Human Fibroblast Cell Line

Figure 8A:
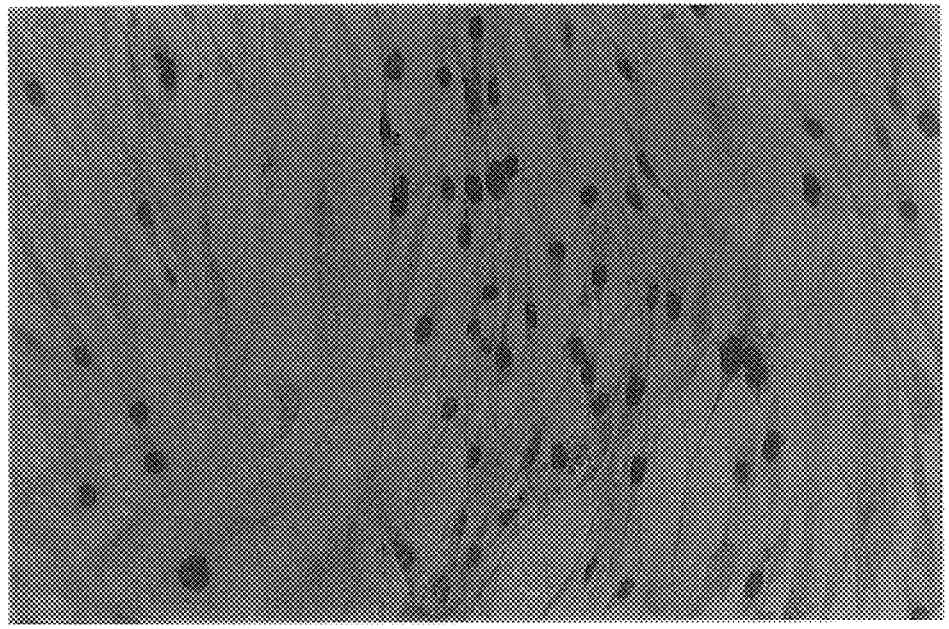
FIGS. 8A and B show the ability of the m89 Rb mutant to suppress the growth of the normal cell WS1.
Figure 8B:
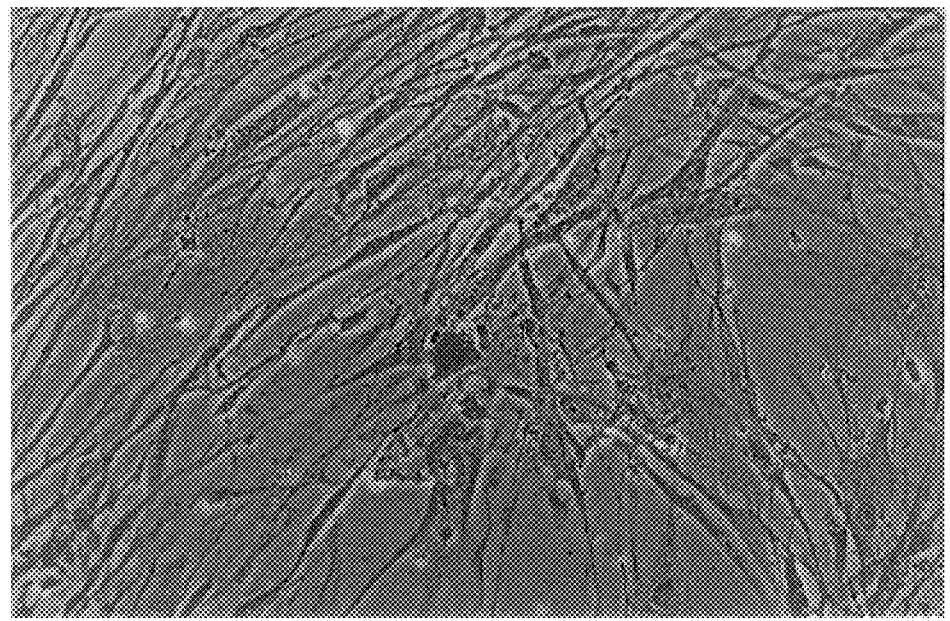

The effect of retinoblastoma cDNA on cell growth was seen as the mutant m89-0 was transfected into the normal human fibroblast cell line WS1. The gene for the SV40 large T antigen was used as a control for the transfection. A plasmid, pPVUO-Neo, which contains the gene for the SV40 large T antigen and a neomycin resistance gene was then transfected in order to monitor the efficiency of transfection. In addition, an inactive mutant form of the Rb gene, "HuBAcpr-1-neo-P16" was used as a control. For transfection, 100 μg of each of the plasmid DNA were mixed with 107 exponentially grown WS1 cells in a final volume of 0.8 ml of RPM1 1640 medium (Gibco) plus 10% FCS in an electroporation chamber unit Cell-Porator™ (BRL). Electroporation was done at 200 volt and 1180 μF. The electroporated cells were allowed to recover at room temperature for 10 minutes and were then diluted in RPM1 1640 plus 10% fetal calf serum (FCS) and plated out in 60 mm dishes at a cell density of 2×104 cells/cm 2. The cells were allowed to attach and grow in the same medium for two days. Thereafter, the medium was changed to RPM1 1640+ 10% FCS+15 ug/ml G418 (GIBCO). Every three days, duplicate dishes were taken for histoimmunochemical staining using either a rabbit polyclonal anti-Rb protein antibodies RB1-ABA1 (FIG. 8A), or with the mouse monoclonal anti-SV40large T antigen antibody Pab 101 (FIG. 8B). As can be seen from FIG. 8A, 13 days after transfection and selection in G418 medium, the WS1 cells expressing the transfected Rb cDNA plasmid m89-0 stained intensely with the anti-Rb protein antibodies. However, the cells that expressed the Rb protein remained as single cells and did not divide. In contrast, cells that expressed the transfected SV40 large T antigen (SVLT) continued to divide into colonies as shown by the group of cells stained positive with the mouse anti SVLT antibody in FIG. 8B. Thus, over expression of the m89-0 Rb cDNA in a cell led to complete arrest of cell growth of the normal cells WS1. Cells transfected with the inactive form of Rb HuβAcpr-1-neo-P16 were not suppressed but divided into colonies.

Figure 9A:
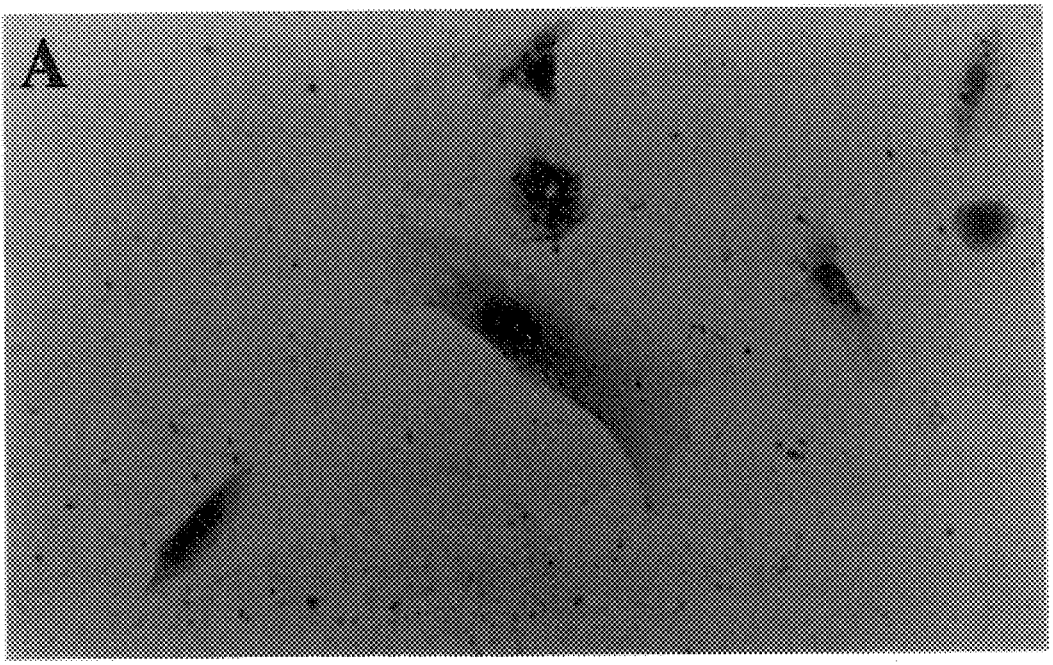
FIGS. 9A and B show the ability of the m89 Rb mutant to suppress the growth of the bladder tumor cell line TCCSUP.
Figure 9B:
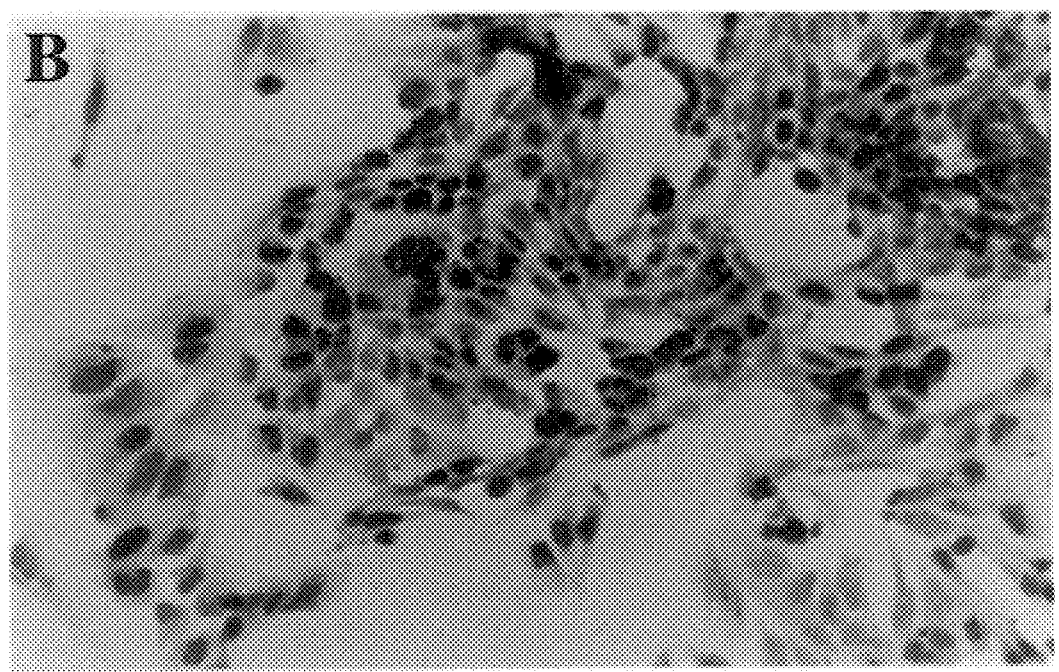

As can be seen in FIG. 9A, cells expressing the transfected m89-0 cDNA failed to divide. In contrast, cells expressing the transfected HuBAcpr-1-neo-P16 divided to form colonies (FIG. 9B). Overexpression of the m89-0 Rb cDNA led to severe retardation of growth of the tumor cells in vitro.

EXAMPLE 17

In addition to the mutants at the regions homologous between Rb and p53, mutations in the p53 protein. Table II lists the partial amino acid sequence of the wild type p53 and conserved amino acid mutants prepared. In addition, Table II lists the DNA sequence corresponding to the mutant amino acid sequence. To prepare the mutants, two primers were synthesized and annealed together. PCR was carried out as described above. As shown in above, the alteration P1, P3 and P5 regions lead to a change in the conformaton of the p53 protein such that it is now capable of binding to its target DNA sequence directly.

TABLE II p53 MUTANTS

P1 WIldTYPE:  ELNEALELK  (SEQ ID NO:4)

CONSERVED a.a. MUTANT (P53-Con P1):  KLYEDFEIE  (SEQ ID NO:10)

(1) 5' GC TCC GAG ATG TTC CGA AAG CTG TAT GAG GAC TTG GAA ATC (SEQ ID NO:11)

GAG GAT GCC CAG GCT GGG 3'

(2) 3' CG AGG CTC TAC AAG GCT TTC GAC ATA CTC CTG AAC CTT TAG (SEQ ID NO:16)

CTC CTA CGG GTC CGA CCC 5'

P3 WILDTYPE:  KKGQSTSRH  (SEQ ID NO:7)

CONSERVED aa MUTANT (P53-Con P3):  NEWFSTARD  (SEQ ID NO:12)

(1) 5' AGC CAC CTG AAG TCC AAC GAG TGG TTC TCT ACC GCC CGC GAT (SEQ ID NO:13)

AAA AAA CTC ATG TTC AAG AC 3'

(2) 3' TCG GTG GAC TTC AGG TTG CTC AGG AAG AGA TGG CGG GCG CTA (SEQ NO ID:17)

TTT TTT GAG TAC AAG TTC TG 5'

P5 WILDTYPE:  KKLMFKTEGPDSD  (SEQ ID NO:9)

Conserved a.a. MUTANT (P53-Con P5):  NEVMWKTKWPDAH  (SEQ ID NO:14)

(1) 5' GTCTACCTCCCGCCAT AACGAA GTCATG TGGAAG ACAAAA TGGCCT  (SEQ ID NO:15)

GACGCA CAC TGACATTCTCCACTTCTT 3'

(2) 3' CAGATGGAGGGCGGTA TTGCTT CAGTAC ACCTTC TGTTTT ACCGGA  (SEQ ID NO:18)

CTGCGT GTG ACTGTAAGAGGTGAAGAA 5'

EXAMPLE 16

Effect of Transfected Plasmids on a Bladder Carcinoma Cell Line

The mutant m89-0 and HuβAcpr-1-neo-P16 plasmids were also transfected into the human bladder carcinoma cells TCCSUP which has no endogenous Rb protein using the same procedures described above. The plasmids used, the methodology for transfection and immunostaining are identical to those described above.

EXAMPLE 18

Generation of the recombinant retrovirus containing a mutant Rb gene.

A Hind III/Bam HI fragment containing the entire coding region of the mutant Rb#89 is subcloned into the Hind III/BgIII sites in a retroviral vector. The resulting plasmid vectors are transfected into the cell line Psi-2. The medium used to culture the transfected cells is infected into another cell line PA317. Cells that produce the recombinant virus were selected in G418 and the retrovirus collected from the medium is concentrated and purified through a sucrose gradient. Mutants of the p53 gene is tested in an identical manner.

EXAMPLE 19
Effect of the G1NaSvRb89 virus on cell proliferation in the eyes

Experimental Proliferative Vitreous Retinopathy (PVR) in rabbits is induced by injection of rabbit fibroblasts and induction of local wound. This procedure consists of inducing a wound at limbus and injecting $2\times10^5$ rabbit fibroblasts into the vitreous under general anesthesia. Post-operatively, the rabbit will receive antibiotic containing local ointment.

Recombinant retroviruses with the mutant Rb or p53 gene are injected into the vitreous ($2\times10^5$ cells/rabbit) with the animal under general anesthesia. Initially, local tolerance of viruses is tested by assessing the maximum dosage of virus (concentration of the virus to be used and the volume of injecting virus). Retroviruses have already been used for injection beneath the retina in mice without reported side effects (Turner and Cepko, Nature 328:132, 1987). The maximum dosage that would not cause side effects will be employed for all subsequent treatment.

The growth of cells in vivo is monitored by photography. The grade of retina detachment is compared with the controls where only a retrovirus containing a 1-Galactosidase gene was injected. Additionally, the growth of cells in vivo is monitored by labelling intra-vitum with BromodeoxyUridine. One hour before euthanasia, the rabbit is given 50 mg/kg BrdU I.V. to label the proliferating cells. After euthanasia, the cells are analyzed for BrdU incorporation into their DNA by immunostaining with antibodies to BrdU. Simultaneously, immunostaining of the cells with antibodies against the Rb or p53 protein or the 1-Galactosidase protein are also performed to assess the efficiency of the infection.

The optimum time for the retrovirus to suppress the growth of the injected cells is assessed by injecting the virus at various time after induction of PVR. The effect of the vitreous on the infection efficiency in rabbit fibroblasts is also determined. The time delay for adding these viruses on rabbit fibroblasts is also determined. The time delay for adding these viruses on rabbit fibroblasts that stimulated with fibroblast growth factors to increase the growth rate is also determined.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

I claim:

1. An isolated DNA molecule, wherein said molecule is a synthetic mutated Rb gene encoding a mutated functionally active retinoblastoma protein, wherein said Rb gene is mutated by changing nucleotides that encode for amino acids in conserved homology regions selected from the group of regions P1(SEQ ID No. 4) P3 (SEQ ID No. 6) and P5 (SEQ ID No. 8) to encode non-conservative amino acids.

2. A plasmid comprising the DNA of claim 1.

* * * * *

UNITED STATES PATENT AND TRADEMARK OFFICE
CERTIFICATE OF CORRECTION

PATENT NO. : 5,969,120
DATED : October 19, 1999
INVENTOR(S) : Yuen Kai Fung

It is certified that error appears in the above-identified patent and that said Letters Patent is hereby corrected as shown below:

In Column 3, line 22, "are" should read --is--.

In Column 4, line 14, "protien" should read --protein--.

In Column 4, line 25, "although" should read --Although--.

In Column 4, line 60, "renders" should read --render--.

In Column 5, line 62, please insert the following sentence at the end of the line. --Figure 2B shows a schematic drawing of the positions of the homology regions on pRb and p53.--.

In Column 5, line 66, "shows" should read --show--.

In Column 6, line 1, "(A)" should read --(4A)--.

In Column 6, line 2, "(B)" should read --(4B)--.

In Column 6, line 44, please insert the word --is-- between the words "gene" and "meant".

In Column 12, line 22, "shematic" should read --schematic--.

UNITED STATES PATENT AND TRADEMARK OFFICE
CERTIFICATE OF CORRECTION

PATENT NO. : 5,969,120
DATED : October 19, 1999
INVENTOR(S) : Yuen Kai Fung

It is certified that error appears in the above-identified patent and that said Letters Patent is hereby corrected as shown below:

In Column 12, line 43, "P3region" should read --P3 region--.

In Column 14, line 13, please delete the comma after "equal".

In Column 15, line 26, "m 89-0" should read --m89-0--.

In Column 15, line 43, "P5 C" should read --P5C--.

In Column 16, line 51, "amount" should read --amounts--.

In Column 17, line 29, "were" should read --was--.

In Column 18, line 40, please remove "the" between the words "is" and "functionally".

UNITED STATES PATENT AND TRADEMARK OFFICE
CERTIFICATE OF CORRECTION

PATENT NO. : 5,969,120
DATED : October 19, 1999
INVENTOR(S) : Yuen Kai Fung

It is certified that error appears in the above-identified patent and that said Letters Patent is hereby corrected as shown below:

In Column 19, line 37, please insert the word --are-- between the words "but" and "not".

In Column 21, line 9, "SV-40large" should read --SV40 large--.

Signed and Sealed this

Twenty-fourth Day of April, 2001

Attest:

NICHOLAS P. GODICI

*Attesting Officer*     Acting Director of the United States Patent and Trademark Office

SEQUENCE LISTING

```
(1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 20
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: internal fragment (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:1:

Leu Leu Ile Lys Pro Arg Tyr Asp Thr Glu Gly Ser Asp Glu Ala
1               5                   10                  15

Asp Gly Ser Lys His
            20
```

(2) INFORMATION FOR SEQ ID NO:2:

(i) SEQUENCE CHARACTERISTICS:
        (A) LENGTH: 20
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: internal fragment (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:2:

Pro Leu Lys Lys Leu Arg Phe Asp Ile Glu Ala Ser Ala Glu Val
1               5                   10                  15

Asp Ala Ser Ile His
            20

(2) INFORMATION FOR SEQ ID NO:3:

(i) SEQUENCE CHARACTERISTICS:
        (A) LENGTH: 20
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: internal fragment (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(ix) FEATURE:
        (A) OTHER INFORMATION:Represents amino acids 871-890
            of the retinoblastoma protein.

(xi) SEQUENCE DESCRIPTION: SEQ ID NO:3:

Pro Leu Lys Lys Leu Arg Phe Asp Ile Glu Gly Ser Asp Glu Ala
1               5                   10                  15

Asp Gly Ser Lys His
            20

(2) INFORMATION FOR SEQ ID NO:4:

(i) SEQUENCE CHARACTERISTICS:
        (A) LENGTH: 9
        (B) TYPE: amino acid
        (C) STRANDEDNESS:

```
            (D) TOPOLOGY: linear (ii) MOLECULE TYPE:
            (A) DESCRIPTION: peptide (iii) HYPOTHETICAL: No (iv) ANTI-SENSE: No (v) FRAGMENT TYPE: internal fragment (vi) ORIGINAL SOURCE:
            (B) STRAIN:
            (C) INDIVIDUAL ISOLATE:
            (D) DEVELOPMENTAL STAGE:
            (F) TISSUE TYPE:
            (G) CELL TYPE:
            (H) CELL LINE:

(ix) FEATURE:
            (A) OTHER INFORMATION:  Represents amino acids 184-192
                of the retinoblastoma protein.

(xi) SEQUENCE DESCRIPTION: SEQ ID NO:4:

Glu Ile Asn Ser Ala Leu Val Leu Lys
1               5

(2) INFORMATION FOR SEQ ID NO:5:

(i) SEQUENCE CHARACTERISTICS:
            (A) LENGTH: 9
            (B) TYPE: amino acid
            (C) STRANDEDNESS:
            (D) TOPOLOGY: linear (ii) MOLECULE TYPE:
            (A) DESCRIPTION: peptide (iii) HYPOTHETICAL: No (iv) ANTI-SENSE: No (v) FRAGMENT TYPE: internal fragment (vi) ORIGINAL SOURCE:
            (B) STRAIN:
            (C) INDIVIDUAL ISOLATE:
            (D) DEVELOPMENTAL STAGE:
            (F) TISSUE TYPE:
            (G) CELL TYPE:
            (H) CELL LINE:

(ix) FEATURE:
            (A) OTHER INFORMATION: Represents amino acids 343-351
                of the p53 protein.

(xi) SEQUENCE DESCRIPTION: SEQ ID NO:5:

Glu Leu Asn Glu Ala Leu Glu Leu Lys
1               5

(2) INFORMATION FOR SEQ ID NO:6:

(i) SEQUENCE CHARACTERISTICS:
            (A) LENGTH: 9
            (B) TYPE: amino acid
            (C) STRANDEDNESS:
            (D) TOPOLOGY: linear (ii) MOLECULE TYPE:
            (A) DESCRIPTION: peptide (iii) HYPOTHETICAL: No (iv) ANTI-SENSE: No (v) FRAGMENT TYPE: internal fragment
```

```
        (vi) ORIGINAL SOURCE:
             (B) STRAIN:
             (C) INDIVIDUAL ISOLATE:
             (D) DEVELOPMENTAL STAGE:
             (F) TISSUE TYPE:
             (G) CELL TYPE:
             (H) CELL LINE:

(ix) FEATURE:
             (A) OTHER INFORMATION: Represents amino acids 245-262
                 of the retinoblastoma protein.

(xi) SEQUENCE DESCRIPTION: SEQ ID NO:6:

Arg Arg Gly Gln Asn Arg Ser Ala Arg
1               5

(2) INFORMATION FOR SEQ ID NO:7:

(i) SEQUENCE CHARACTERISTICS:
             (A) LENGTH: 9
             (B) TYPE: amino acid
             (C) STRANDEDNESS:
             (D) TOPOLOGY: linear (ii) MOLECULE TYPE:
             (A) DESCRIPTION: peptide (iii) HYPOTHETICAL: No (iv) ANTI-SENSE: No (v) FRAGMENT TYPE: internal fragment (vi) ORIGINAL SOURCE:
             (B) STRAIN:
             (C) INDIVIDUAL ISOLATE:
             (D) DEVELOPMENTAL STAGE:
             (F) TISSUE TYPE:
             (G) CELL TYPE:
             (H) CELL LINE:

(ix) FEATURE:
             (A) OTHER INFORMATION: Represents amino acids 372-380
                 of the p53 protein.

(xi) SEQUENCE DESCRIPTION: SEQ ID NO:7:

Lys Lys Gly Gln Ser Thr Ser Arg His
1               5

(2) INFORMATION FOR SEQ ID NO:8:

(i) SEQUENCE CHARACTERISTICS:
             (A) LENGTH: 14
             (B) TYPE: amino acid
             (C) STRANDEDNESS:
             (D) TOPOLOGY: linear (ii) MOLECULE TYPE:
             (A) DESCRIPTION: peptide (iii) HYPOTHETICAL: No (iv) ANTI-SENSE: No (v) FRAGMENT TYPE: internal fragment (vi) ORIGINAL SOURCE:
             (B) STRAIN:
             (C) INDIVIDUAL ISOLATE:
             (D) DEVELOPMENTAL STAGE:
             (F) TISSUE TYPE:
             (G) CELL TYPE:
             (H) CELL LINE:

(ix) FEATURE:
```

(A) OTHER INFORMATION: Represents amino acids 873-886
                of the retinoblastoma protein.

(xi) SEQUENCE DESCRIPTION: SEQ ID NO:8:

Lys Lys Leu Arg Phe Asp Ile Glu Gly Ser Asp Glu Ala Asp
1               5                   10

(2) INFORMATION FOR SEQ ID NO:9:

(i) SEQUENCE CHARACTERISTICS:
            (A) LENGTH: 13
            (B) TYPE: amino acid
            (C) STRANDEDNESS:
            (D) TOPOLOGY: linear (ii) MOLECULE TYPE:
            (A) DESCRIPTION: peptide (iii) HYPOTHETICAL: No (iv) ANTI-SENSE: No (v) FRAGMENT TYPE: internal fragment (vi) ORIGINAL SOURCE:
            (B) STRAIN:
            (C) INDIVIDUAL ISOLATE:
            (D) DEVELOPMENTAL STAGE:
            (F) TISSUE TYPE:
            (G) CELL TYPE:
            (H) CELL LINE:

(ix) FEATURE:
            (A) OTHER INFORMATION: Represents amino acids 381-393
                of the p53 protein.

(xi) SEQUENCE DESCRIPTION: SEQ ID NO:9:

Lys Lys Leu Met Phe Lys Thr Glu Gly Pro Asp Ser Asp
1               5                   10

(2) INFORMATION FOR SEQ ID NO:10:

(i) SEQUENCE CHARACTERISTICS:
            (A) LENGTH: 9
            (B) TYPE: amino acid
            (C) STRANDEDNESS:
            (D) TOPOLOGY: linear (ii) MOLECULE TYPE:
            (A) DESCRIPTION: peptide (iii) HYPOTHETICAL: No (iv) ANTI-SENSE: No (v) FRAGMENT TYPE: internal fragment (vi) ORIGINAL SOURCE:
            (B) STRAIN:
            (C) INDIVIDUAL ISOLATE:
            (D) DEVELOPMENTAL STAGE:
            (F) TISSUE TYPE:
            (G) CELL TYPE:
            (H) CELL LINE:

(ix) FEATURE:
            (A) OTHER INFORMATION: Represents mutant protein of
                amino acids 343-351 of the p53 protein.

(xi) SEQUENCE DESCRIPTION: SEQ ID NO:10:

Lys Leu Tyr Glu Asp Phe Glu Ile Glu
1               5

(2) INFORMATION FOR SEQ ID NO:11:

```
    (i) SEQUENCE CHARACTERISTICS:
        (A) LENGTH: 59
        (B) TYPE: nucleic acid
        (C) STRANDEDNESS: double stranded
        (D) TOPOLOGY: linear (ii) MOLECULE TYPE:
        (A) DESCRIPTION: other (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(ix) FEATURE:
        (A) OTHER INFORMATION: Represents nucleic acids
            encoding mutant protein of sequence ID No. 10.

(xi) SEQUENCE DESCRIPTION: SEQ ID NO:11:

GCTCCGAGAT GTTCCGAAAG CTGTATGAGG ACTTGGAAAT CGAGGATCGG           50

CAGGCTGGG                                                       59

(2) INFORMATION FOR SEQ ID NO:12:

(i) SEQUENCE CHARACTERISTICS:
        (A) LENGTH: 9
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: internal fragment (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(ix) FEATURE:
        (A) OTHER INFORMATION: Represents mutant protein of
            amino acids 372-380 of the p53 protein.

(xi) SEQUENCE DESCRIPTION: SEQ ID NO:12:

Asn Glu Trp Phe Ser Thr Ala Arg Asp
1               5

(2) INFORMATION FOR SEQ ID NO:13:

(i) SEQUENCE CHARACTERISTICS:
        (A) LENGTH: 62
        (B) TYPE: nucleic acid
        (C) STRANDEDNESS: double stranded
        (D) TOPOLOGY: linear (ii) MOLECULE TYPE:
        (A) DESCRIPTION: other (iii) HYPOTHETICAL: No
```

(iv) ANTI-SENSE: No (vi) ORIGINAL SOURCE:
             (B) STRAIN:
             (C) INDIVIDUAL ISOLATE:
             (D) DEVELOPMENTAL STAGE:
             (F) TISSUE TYPE:
             (G) CELL TYPE:
             (H) CELL LINE:

(ix) FEATURE:
             (A) OTHER INFORMATION: Represents nucleic acids
                 encoding mutant protein of sequence ID No. 12.

(xi) SEQUENCE DESCRIPTION: SEQ ID NO:13:

AGCCACCTGA AGTCCAACGA GTGGTTCTCT ACCGCCCGCG ATAAAAAACT          50

CATGTTCAAG AC                                                   62

(2) INFORMATION FOR SEQ ID NO:14:

(i) SEQUENCE CHARACTERISTICS:
             (A) LENGTH: 13
             (B) TYPE: amino acid
             (C) STRANDEDNESS:
             (D) TOPOLOGY: linear (ii) MOLECULE TYPE:
             (A) DESCRIPTION: peptide (iii) HYPOTHETICAL: No (iv) ANTI-SENSE: No (v) FRAGMENT TYPE: internal fragment (vi) ORIGINAL SOURCE:
             (B) STRAIN:
             (C) INDIVIDUAL ISOLATE:
             (D) DEVELOPMENTAL STAGE:
             (F) TISSUE TYPE:
             (G) CELL TYPE:
             (H) CELL LINE:

(ix) FEATURE:
             (A) OTHER INFORMATION: Represents mutant protein of
                 amino acids 381-393 of the p53 protein.

(xi) SEQUENCE DESCRIPTION: SEQ ID NO:14:

Asn Glu Val Met Trp Lys Thr Lys Trp Pro Asp Ala His
1               5                   10

(2) INFORMATION FOR SEQ ID NO:15:

(i) SEQUENCE CHARACTERISTICS:
             (A) LENGTH: 73
             (B) TYPE: nucleic acid
             (C) STRANDEDNESS: double stranded
             (D) TOPOLOGY: linear (ii) MOLECULE TYPE:
             (A) DESCRIPTION: other (iii) HYPOTHETICAL: No (iv) ANTI-SENSE: No (vi) ORIGINAL SOURCE:
             (B) STRAIN:
             (C) INDIVIDUAL ISOLATE:
             (D) DEVELOPMENTAL STAGE:
             (F) TISSUE TYPE:
             (G) CELL TYPE:
             (H) CELL LINE:

```
        (ix) FEATURE:
             (A) OTHER INFORMATION: Represents nucleic acids
                 encoding mutant protein of sequence ID No. 14.

(xi) SEQUENCE DESCRIPTION: SEQ ID NO:15:

GTCTACCTCC CGCCATAACG AAGTCATGTG GAAGACAAAA TGGCCTGACG             50

CACACTGACA TTCTCCACTT CTT                                         73

(2) INFORMATION FOR SEQ ID NO:16:

(i) SEQUENCE CHARACTERISTICS:
             (A) LENGTH: 59
             (B) TYPE: nucleic acid
             (C) STRANDEDNESS: double stranded
             (D) TOPOLOGY: linear (ii) MOLECULE TYPE:
             (A) DESCRIPTION: other (iii) HYPOTHETICAL: No (iv) ANTI-SENSE: No (vi) ORIGINAL SOURCE:
             (B) STRAIN:
             (C) INDIVIDUAL ISOLATE:
             (D) DEVELOPMENTAL STAGE:
             (F) TISSUE TYPE:
             (G) CELL TYPE:
             (H) CELL LINE:

(ix) FEATURE:

(xi) SEQUENCE DESCRIPTION: SEQ ID NO:16:

CCCAGCCTGG GCATCCTCGA TTTCCAAGTC CTCATACAGC TTTCGGAACA             50

TCTCGGAGC                                                         59

(2) INFORMATION FOR SEQ ID NO:17:

(i) SEQUENCE CHARACTERISTICS:
             (A) LENGTH: 62
             (B) TYPE: nucleic acid
             (C) STRANDEDNESS: double stranded
             (D) TOPOLOGY: linear (ii) MOLECULE TYPE:
             (A) DESCRIPTION: other (iii) HYPOTHETICAL: No (iv) ANTI-SENSE: No (vi) ORIGINAL SOURCE:
             (B) STRAIN:
             (C) INDIVIDUAL ISOLATE:
             (D) DEVELOPMENTAL STAGE:
             (F) TISSUE TYPE:
             (G) CELL TYPE:
             (H) CELL LINE:

(ix) FEATURE:

(xi) SEQUENCE DESCRIPTION: SEQ ID NO:17:

TGCTTGAACA TGAGTTTTTT ATCGCGGGCG GTAGAGAAGG ACTCGTTGGA             50

CTTCAGGTGG CT                                                     62

(2) INFORMATION FOR SEQ ID NO:18:

(i) SEQUENCE CHARACTERISTICS:
             (A) LENGTH: 73
             (B) TYPE: nucleic acid
```

(C) STRANDEDNESS: double stranded
            (D) TOPOLOGY: linear (ii) MOLECULE TYPE:
            (A) DESCRIPTION: other (iii) HYPOTHETICAL: No (iv) ANTI-SENSE: No (vi) ORIGINAL SOURCE:
            (B) STRAIN:
            (C) INDIVIDUAL ISOLATE:
            (D) DEVELOPMENTAL STAGE:
            (F) TISSUE TYPE:
            (G) CELL TYPE:
            (H) CELL LINE:

(ix) FEATURE:

(xi) SEQUENCE DESCRIPTION: SEQ ID NO:18:

AAGAAGTGGA GAATGTCAGT GTGCGTCAGG CCATTTTGTC TTCCACATGA                50

CTTCGTTATG GCGGGAGGTA GAC                                              73

(2) INFORMATION FOR SEQ ID NO:19:

(i) SEQUENCE CHARACTERISTICS:
            (A) LENGTH: 12
            (B) TYPE: nucleic acid
            (C) STRANDEDNESS: double stranded
            (D) TOPOLOGY: linear (ii) MOLECULE TYPE:
            (A) DESCRIPTION: other (iii) HYPOTHETICAL: No (iv) ANTI-SENSE: No (vi) ORIGINAL SOURCE:
            (B) STRAIN:
            (C) INDIVIDUAL ISOLATE:
            (D) DEVELOPMENTAL STAGE:
            (F) TISSUE TYPE:
            (G) CELL TYPE:
            (H) CELL LINE:

(ix) FEATURE:

(xi) SEQUENCE DESCRIPTION: SEQ ID NO:19:

CGGATCCGCG TC                                                          12